(12) United States Patent
Docherty et al.

(10) Patent No.: US 11,980,593 B2
(45) Date of Patent: *May 14, 2024

(54) COMPOSITIONS AND METHODS FOR TREATING HYPERTENSION

(71) Applicant: POVIVA CORP, Carson City, NV (US)

(72) Inventors: John Docherty, Port Perry (CA); Christopher Andrew Bunka, Kelowna (CA)

(73) Assignee: POVIVA CORP., Carson City, NV (US)

( * ) Notice: Subject to any disclaimer, the term of this patent is extended or adjusted under 35 U.S.C. 154(b) by 8 days.

This patent is subject to a terminal disclaimer.

(21) Appl. No.: 17/857,991

(22) Filed: Jul. 5, 2022

(65) Prior Publication Data
US 2024/0009141 A1    Jan. 11, 2024

(51) Int. Cl.
| | |
|---|---|
| A61K 31/05 | (2006.01) |
| A23D 9/007 | (2006.01) |
| A23L 33/00 | (2016.01) |
| A23L 33/105 | (2016.01) |
| A23L 33/115 | (2016.01) |
| A61K 9/00 | (2006.01) |
| A61K 47/36 | (2006.01) |
| A61K 47/44 | (2017.01) |

(52) U.S. Cl.
CPC .............. *A61K 31/05* (2013.01); *A23D 9/007* (2013.01); *A23L 33/105* (2016.08); *A23L 33/115* (2016.08); *A23L 33/40* (2016.08); *A61K 9/0056* (2013.01); *A61K 47/36* (2013.01); *A61K 47/44* (2013.01); *A23V 2002/00* (2013.01)

(58) Field of Classification Search
CPC ...... A61K 31/05; A61K 9/0056; A61K 47/36; A61K 47/44; A23D 9/007; A23L 33/105; A23L 33/115; A23L 33/40; A23V 2002/00
See application file for complete search history.

(56) References Cited

U.S. PATENT DOCUMENTS

| | | | |
|---|---|---|---|
| 11,504,350 B2 | 11/2022 | Levine et al. | |
| 11,666,543 B1 * | 6/2023 | Docherty | A61K 36/185 514/731 |
| 11,666,544 B1 * | 6/2023 | Docherty | A61K 31/575 424/725 |
| 2021/0128519 A1 | 5/2021 | Cohen et al. | |
| 2021/0145036 A1 * | 5/2021 | Docherty | A61K 36/31 |
| 2021/0299062 A1 | 9/2021 | Rosenfeld | |
| 2021/0330683 A1 * | 10/2021 | Docherty | A61K 31/7072 |
| 2022/0160731 A1 * | 5/2022 | Docherty | A61K 47/36 |
| 2022/0193003 A1 | 6/2022 | Alugupalli et al. | |
| 2022/0265743 A1 | 8/2022 | Lecht et al. | |

FOREIGN PATENT DOCUMENTS

| | | | |
|---|---|---|---|
| CN | 1102689843 A | 9/2019 | |
| CN | 114245739 A | 3/2022 | |
| TW | 201801721 A | 1/2018 | |
| WO | WO-2020236802 A1 * | 11/2020 | ............. A61K 31/05 |

OTHER PUBLICATIONS

O'Sullivan SE. An update on PPAR activation by cannabinoids. Br J Pharmacol. Jun. 2016;173(12):1899-910. doi: 10.1111/bph.13497. Epub May 19, 2016. PMID: 27077495; PMCID: PMC4882496. (Year: 2016).*
U.S. Appl. No. 17/857,985, filed Jul. 5, 2022 and co-pending; Office Action dated Sep. 13, 2022.
U.S. Appl. No. 17/857,985, filed Jul. 5, 2022 and co-pending; Examiner's Interview Summary date Nov. 28, 2022.
Alfulaij, N et al., "Cannabinoids, the Heart of the Matter," J. Am. Heart Assoc 13: 7(14) (2018).
Atalay, S et al., "Antioxidative and Anti-Inflammatory Properties of Cannabidiol," Antioxidants 9(1):21 (2019).
Malinowska, B et al., "Triphasic blood pressure responses to cannabinoids: do we understand the mechanism?" Br J Pharmacol. 165(7):2073-88 (2012).
Kendall, DA et al., "Cannabinoid Receptors in the Central Nervous System: Their signaling and Roles in Disease," Front Cell Neurosci. 10:294 (2017).
Pacher, P et al., "The endocannabinoid system as an emerging target of pharmacotherapy," Pharmcol Rev. 58:389-462 (2006).
Patrician, A et al., "Examination of a new delivery approach for oral cannabidiol in healthy subjects: a randomized, double-blinded, placebo-controlled pharmacokinetics study," Advances in Therapy 36(11):3196-3210 (2018).
Richter, JS et al., "A Systematic Review of the Complex Effects of Cannabinoids on Cerebral and Peripheral Circulation Animal Models,"Front Physiol. 9:622 (2018).
Ruiz-Valdepenas, L et al. "Connabidiol reduces lipopolysaccharide-induce vascular changes and inflammation in the mouse brain," J Neuroinflammation 8(1):5 (2011).
Sultan, SR et al. "A Systematic Review and Meta-Analysis of the Haemodynamic Effects of Cannabidiol," Front. Pharmacol. 8:81 (2017).
Sultan, SR e al., "The effects of acute and sustained cannabidiol dosing for seven days on the haemodynamics in healthy men: A randomized controlled trial," British J. Cin. Pharmacol. 86:1125-1138 (2020).

* cited by examiner

*Primary Examiner* — Robert H Havlin
*Assistant Examiner* — Chantal Adlam
(74) *Attorney, Agent, or Firm* — FisherBroyles LLP; Anthony J DoVale

(57) ABSTRACT

Disclosed herein are compositions and methods for delivering cannabidiol to subject in need of hypertension treatment. The disclosed compositions are orally delivered. Further disclosed are kits comprising the disclosed compositions as part of a method of delivering the cannabidiol-containing compositions.

20 Claims, 13 Drawing Sheets

COMPOSITIONS AND METHODS FOR TREATING HYPERTENSION

FIELD

Disclosed herein are compositions and methods for delivering cannabidiol to subject in need of hypertension treatment. The disclosed compositions are orally delivered. Further disclosed are kits comprising the disclosed compositions as part of a method of delivering the cannabidiol-containing compositions.

DETAILED DESCRIPTION OF THE DISCLOSURE

Figure 1:
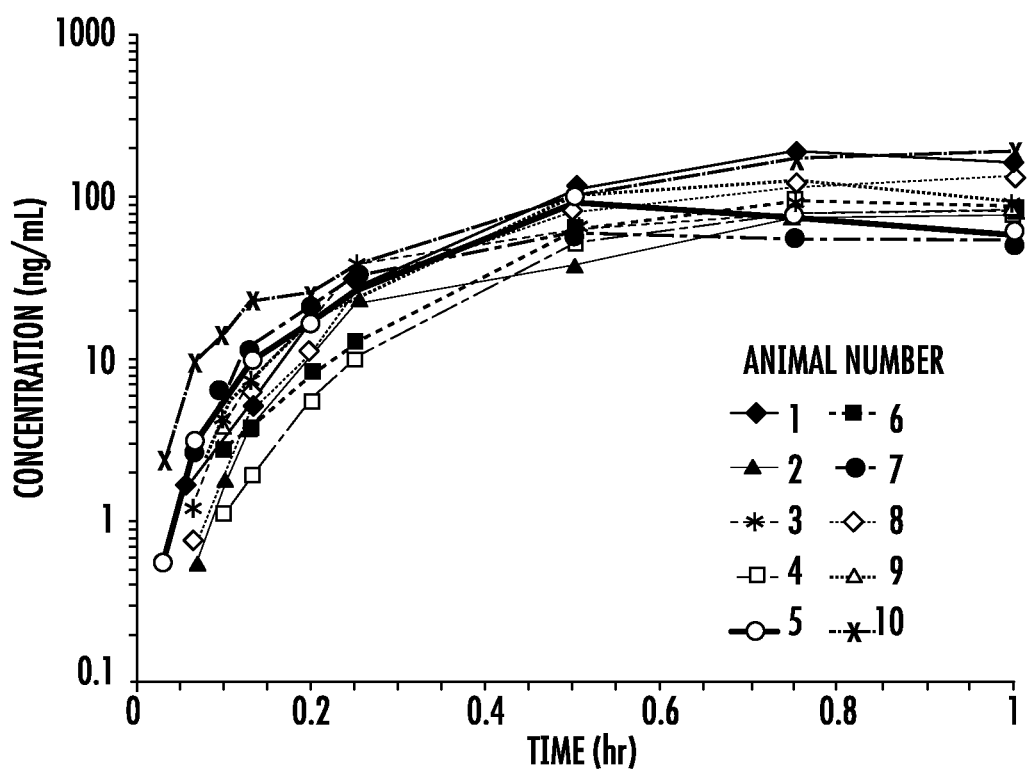
FIG. 1 is a plot of the individual plasma concentration of CBD in Animals 1-10 after oral administration of 25 mg/kg of the composition disclosed in Table 1.
Figure 2:
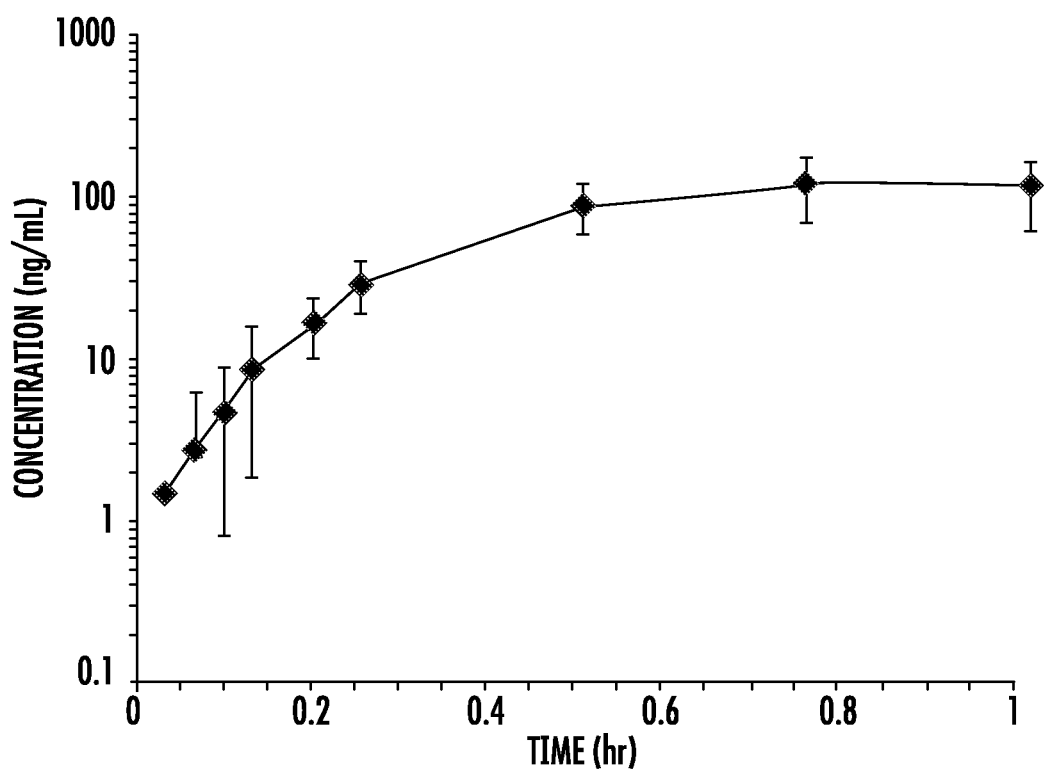
FIG. 2 is the plot of the average plasma concentrations of CBD in Animals 1-10 after oral administration of 25 mg/kg of the composition disclosed in Table 1.
Figure 3:
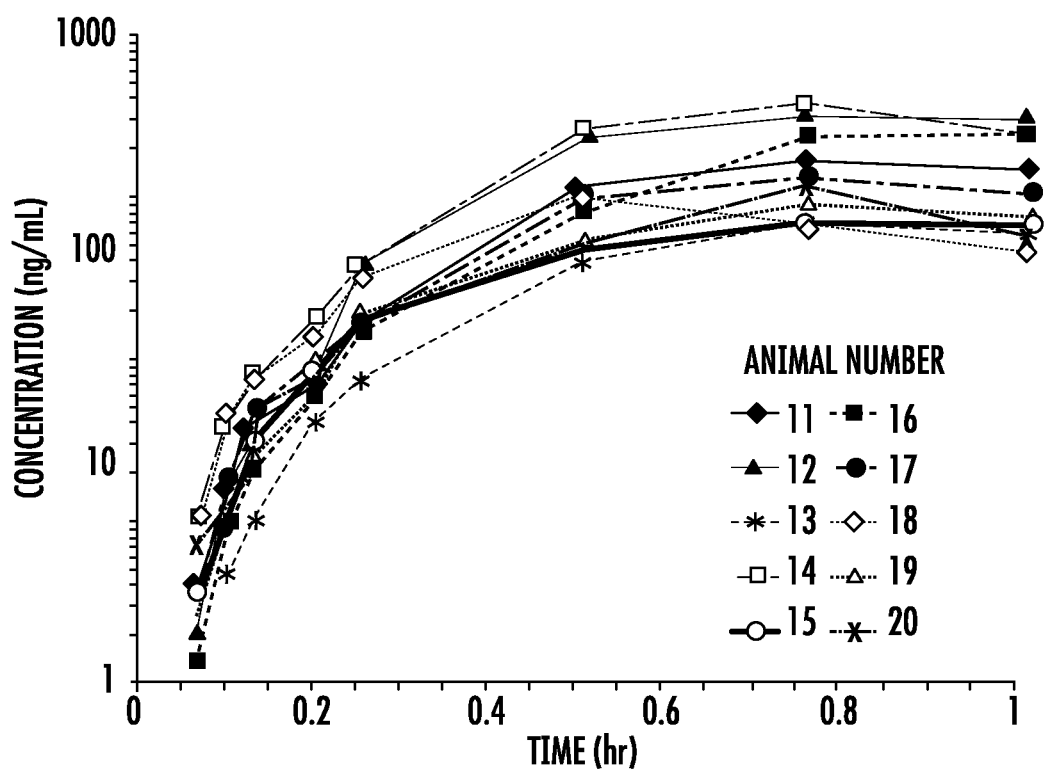
FIG. 3 is a plot of the individual plasma concentration of CBD in Animals 11-20 after oral administration of 25 mg/kg of the composition disclosed in Table 2.
Figure 4:
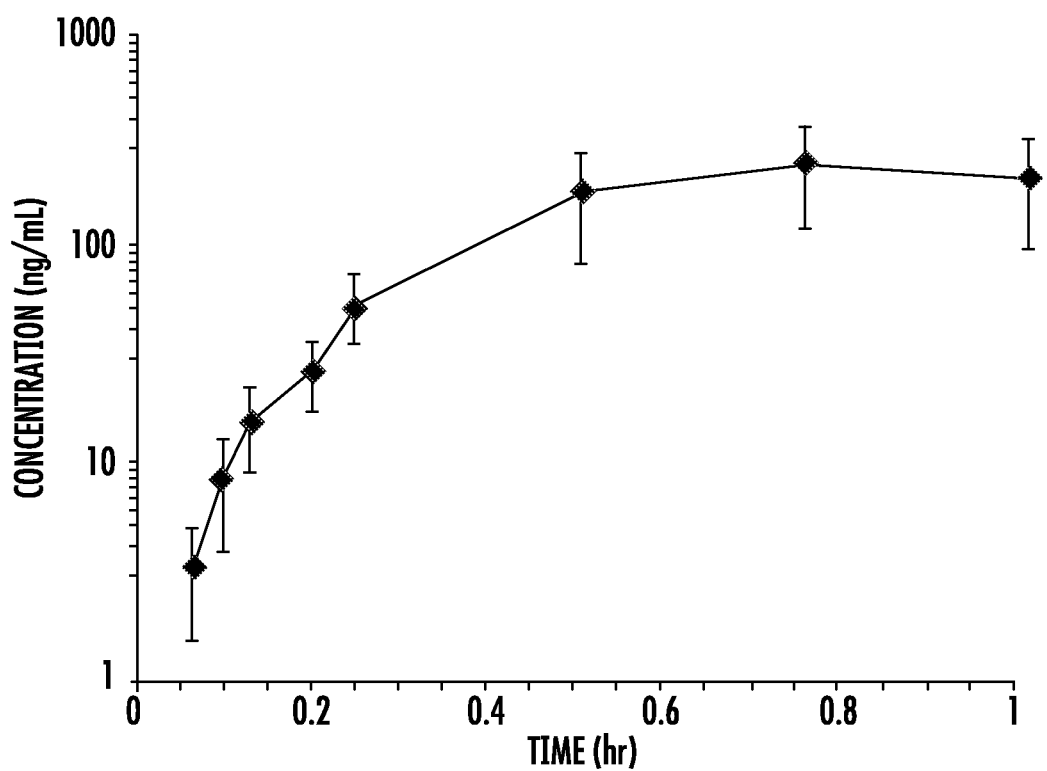
FIG. 4 is the plot of the average plasma concentrations of CBD in Animals 11-20 after oral administration of 25 mg/kg of the composition disclosed in Table 2.
Figure 5:
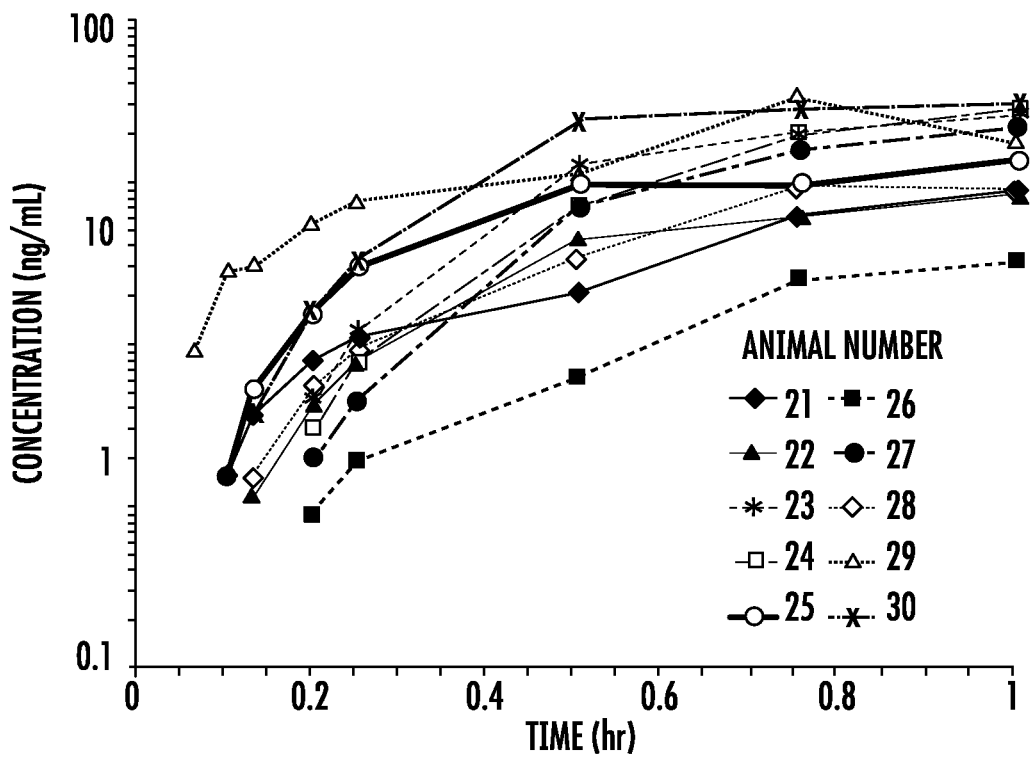
FIG. 5 is a plot of the individual plasma concentration of CBD in Animals 21-30 after oral administration of 25 mg/kg of the composition disclosed in Table 3.
Figure 6:
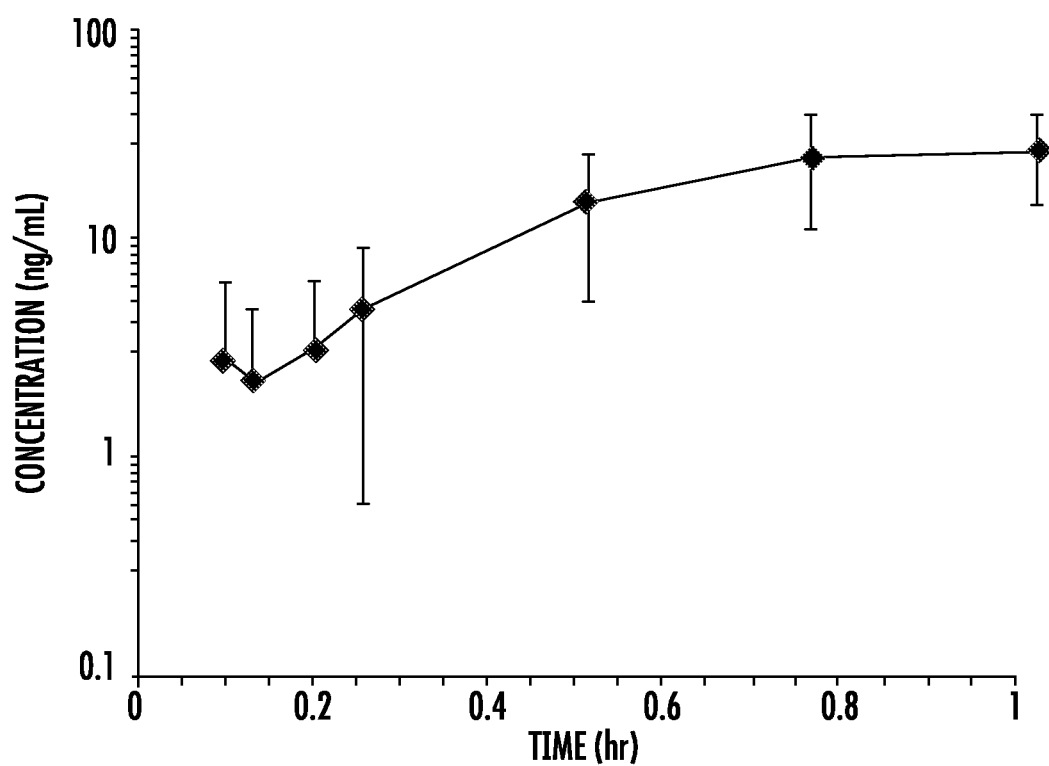
FIG. 6 is the plot of the average plasma concentrations of CBD in Animals 21-30 after oral administration of 25 mg/kg of the composition disclosed in Table 3.
Figure 7:
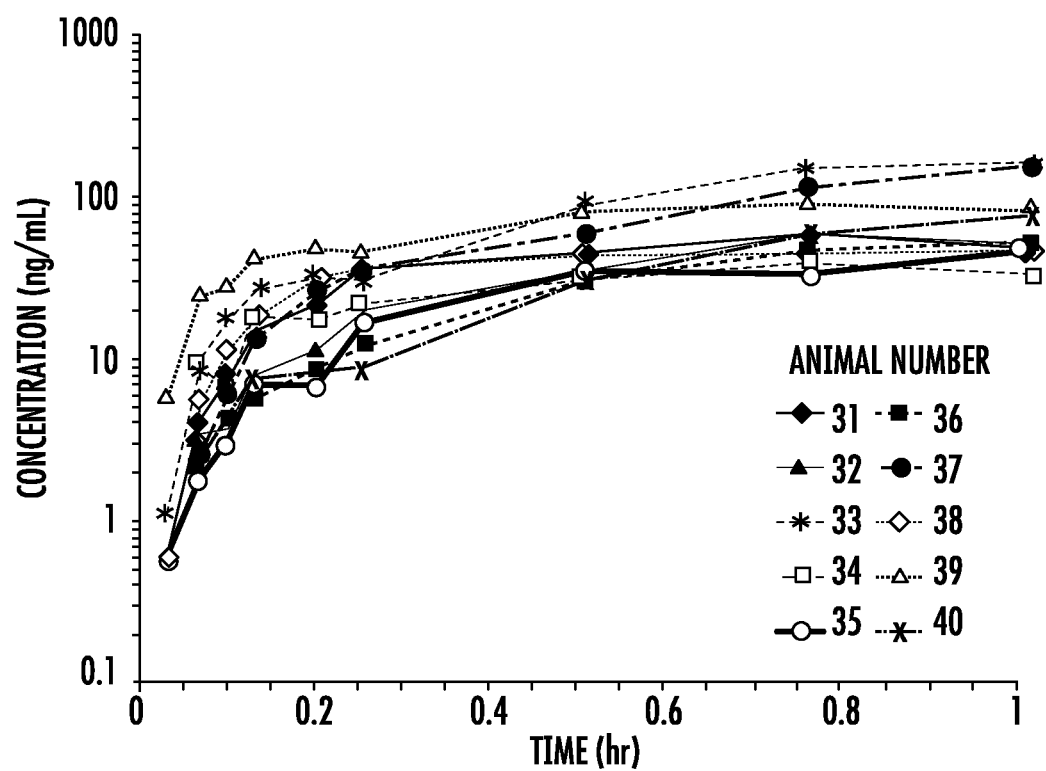
FIG. 7 is a plot of the individual plasma concentration of CBD in Animals 31-40 after oral administration of 25 mg/kg of the composition disclosed in Table 4.
Figure 8:
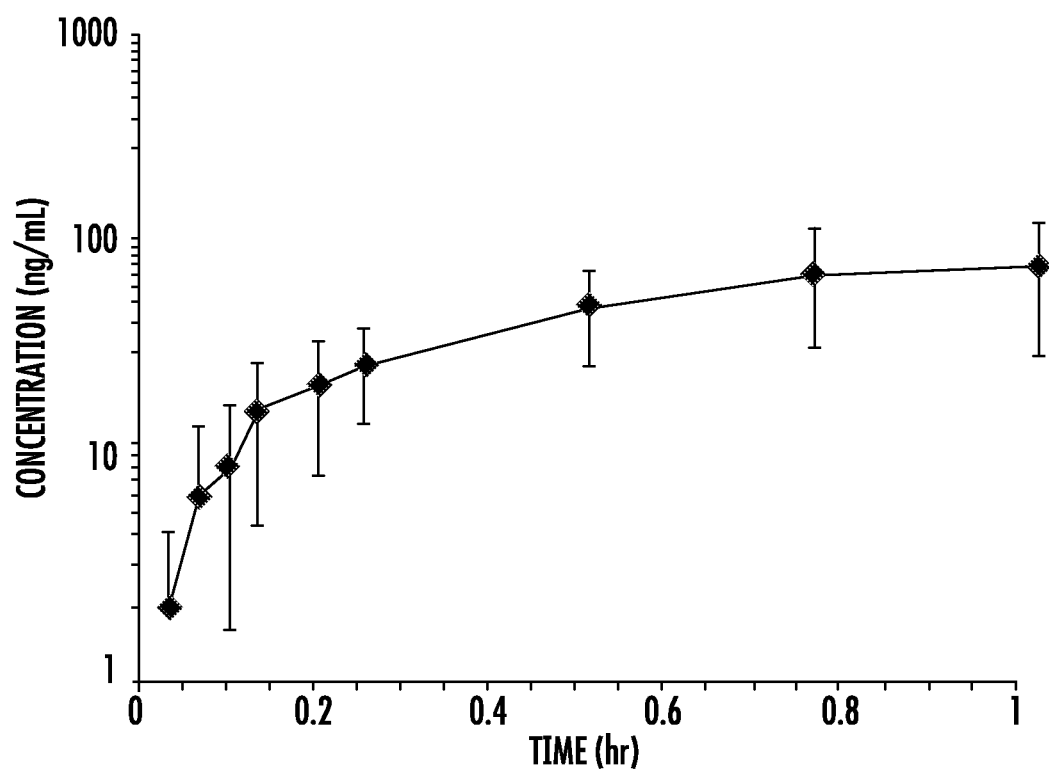
FIG. 8 is the plot of the average plasma concentrations of CBD in Animals 31-40 after oral administration of 25 mg/kg of the composition disclosed in Table 4.
Figure 9:
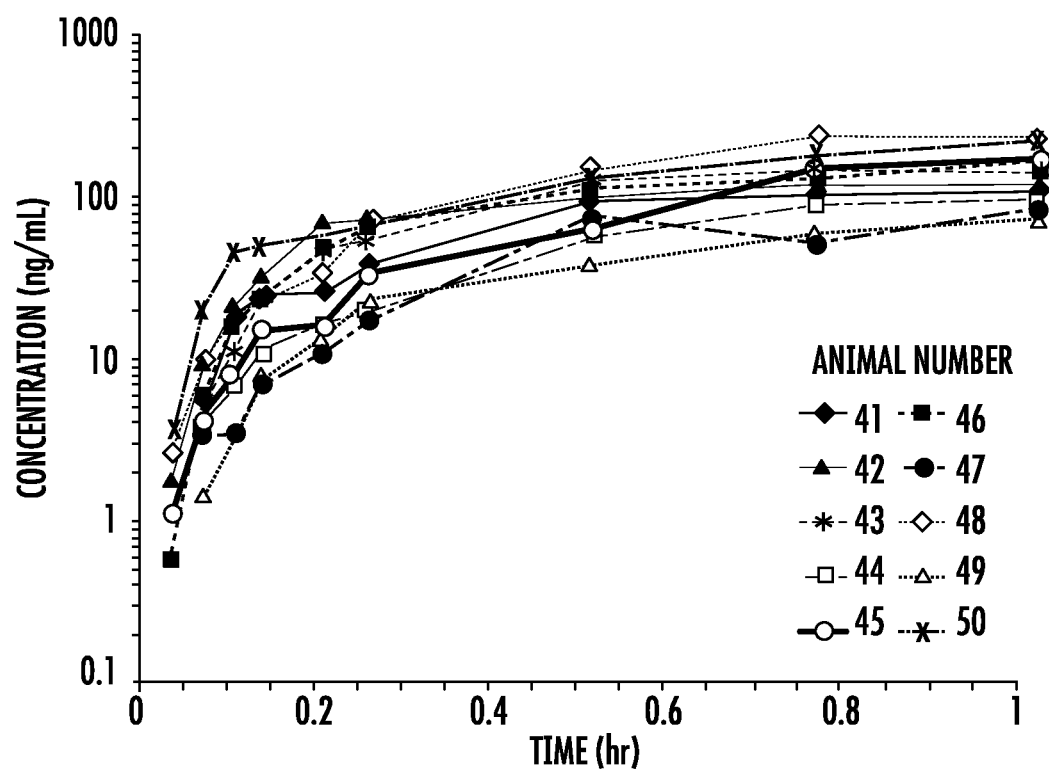
FIG. 9 is a plot of the individual plasma concentration of CBD in Animals 41-50 after oral administration of 25 mg/kg of the composition disclosed in Table 5.
Figure 10:
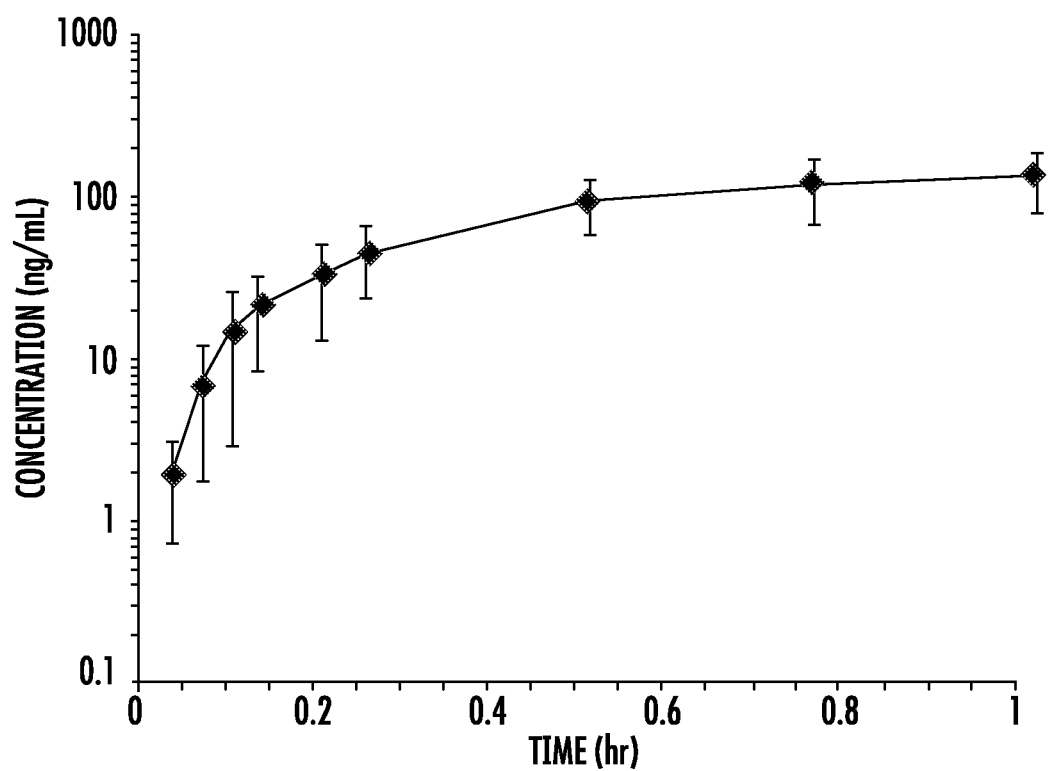
FIG. 10 is the plot of the average plasma concentrations of CBD in Animals 41-50 after oral administration of 25 mg/kg of the composition disclosed in Table 5.

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The term "composition" is defined herein as a composition that does not require approval by a regulatory authority an can be offered for sale by any retail merchant, for example, pharmacies, grocery stores, convenience stores, department stores, and the like.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Compositions

In one aspect disclosed compositions comprise:
A) a base composition; and
B) one or more delivery agents.

Base Compositions

According to the present disclosure the base compositions can comprise CBD oil. What is meant herein by the term "CBD oil" is the cannabidiol-containing extract from the hemp plant *Cannabis sativa*. The CBD oil useful for preparing the disclosed compositions can be extracts which are crude extracts containing less than about 80% by weight of cannabidiol. As used herein CBD oil comprising less than about 80% by weight of cannabidiol is referred to a "crude CBD oil." When using lower percentage extracts the formulator will necessarily adjust the amount of CBD oil present in the disclosed compositions to ensure adequate delivery of the desired amount of cannabidiol.

In one embodiment, the compositions comprise a "hemp distillate" comprising from about 80% to about 92% by weight of cannabidiol. In a still further embodiment isolated, pure cannabidiol can be used in the present compositions. When the hemp distillate comprising from 80% to about 92% by weight cannabidiol is used, the term "CBD oil" applies. In some descriptions of the "CBD oil" this ingredient can be referred to as a "CBD resin."

Another aspect of the present disclosure relates the base compositions, comprise:
a) from about 0.5% to about 20% by weight of CBD oil;
b) from about 0.5% to about 60% by weight of one or more edible oils; and
c) the balance a carrier.

In another embodiment of this aspect the base compositions, comprise:
a) from about 0.5% to about 20% by weight of CBD oil;
b) from about 0.5% to about 60% by weight of one or more edible oils; and
c) the balance from about 20% to about 99% by weight of a carrier chosen from gum Arabic, inulin, microcrystalline cellulose, D-lactose monohydrate, quillaia, xanthan gum, pectin, guar, and psyllium.

In one embodiment of this aspect the compositions, comprise:
a) from about 2% to about 5% by weight of CBD oil;
b) from about 4% to about 15% by weight of sunflower oil; and
c) a carrier chosen from gum Arabic, inulin, microcrystalline cellulose, D-lactose monohydrate, quillaia, xanthan gum, pectin, guar, and psyllium.

In a non-limiting example of this iteration the base compositions, comprise:
a) from about 2% to about 5% by weight of CBD oil;
b) from about 6% to about 15% by weight of sunflower oil;
c) from about 5% to about 20% of a bile salt; and
d) from about a carrier chosen from gum Arabic, inulin, microcrystalline cellulose, D-lactose monohydrate, and quillaia.

In a further example the carrier is gum Arabic. In another example the carrier is inulin. In a yet another example the carrier is microcrystalline cellulose. In a still further example the carrier is D-lactose monohydrate. In a still another example the carrier is quillaia.

In a further embodiment of this aspect the base compositions, comprise:
a) from about 0.5% to about 8% by weight of CBD oil;
b) from about 0.5% to about 15% by weight of coconut oil; and
c) a carrier chosen from gum Arabic, inulin, microcrystalline cellulose, D-lactose monohydrate, quillaia, xanthan gum, pectin, guar, and psyllium.

In a further iteration of this embodiment the base compositions, comprise:
a) from about 2% to about 5% by weight of CBD oil;
b) from about 4% to about 15% by weight of coconut oil; and
c) a carrier chosen from gum Arabic, inulin, microcrystalline cellulose, D-lactose monohydrate, quillaia, xanthan gum, pectin, guar, and psyllium.

In a non-limiting example of this iteration the base compositions, comprise:
a) from about 2% to about 5% by weight of CBD oil;
b) from about 0.5% to about 15% by weight of coconut oil;
c) from about 5% to about 15% of a bile salt; and
d) a carrier chosen from gum Arabic, inulin, microcrystalline cellulose, D-lactose monohydrate, and quillaia.

In one embodiment of this aspect, the base composition comprises:
a) from about 0.5% to about 8% by weight of CBD oil;
b) from about 0.5% to about 15% by weight of coconut oil; and
c) a carrier chosen from gum Arabic, inulin, microcrystalline cellulose, D-lactose monohydrate, quillaia, xanthan gum, pectin, guar, and psyllium.

In a further embodiment of this aspect the base compositions, comprise:
a) from about 0.5% to about 8% by weight of CBD oil;
b) from about 0.5% to about 15% by weight of coconut oil; and
c) a carrier chosen from gum Arabic, inulin, microcrystalline cellulose, D-lactose monohydrate, quillaia, xanthan gum, pectin, guar, and psyllium.

In a further iteration of this embodiment the base compositions, comprise:
a) from about 2% to about 5% by weight of CBD oil;
b) from about 4% to about 15% by weight of coconut oil; and
c) a carrier chosen from gum Arabic, inulin, microcrystalline cellulose, D-lactose monohydrate, quillaia, xanthan gum, pectin, guar, and psyllium.

In a non-limiting example of this iteration the base compositions, comprise:
a) from about 2% to about 5% by weight of CBD oil;
b) from about 0.5% to about 15% by weight of coconut oil;
c) from about 5% to about 15% of a bile salt; and
d) a carrier chosen from gum Arabic, inulin, microcrystalline cellulose, D-lactose monohydrate, and quillaia.

The disclosed compositions comprise from about 0.5% to about 20% by weight of CBD oil. In one embodiment the disclosed base compositions can comprise from about 0.5% to about 8% by weight of CBD oil. In one embodiment, the base composition can comprise from about 1% to about 5% by weight of CBD oil. In another embodiment, the base composition can comprise from about 2% to about 6% by weight of CBD oil. In a further embodiment, the base composition can comprise from about 2% to about 5% by weight of CBD oil. In a yet further embodiment, the base composition can comprise from about 3% to about 5% by weight of CBD oil. For example, the amount of CBD oil can be 0.5%, 0.6%, 0.7%, 0.8%, 0.9%, 1%, 2%, 3%, 4%, 5%, 6%, 7%, or 8%% by weight or any fractional amounts, for example, 1.5%, 3.25%, and 5.75%.

The addition of a carboxylic acid in some embodiments aid in the formulation a flowable powder for encapsulation or packaging as described herein below, especially when the carboxylic acid serves to form a salt with one or more of the carriers or delivery agents.

The disclosed anti-hypertension compositions, comprise:
a) from about 5 mg to about 15 mg by weight of CBD oil; and
b) from about 5 mg to about 45 mg by weight of one or more edible oils.

In one aspect the disclosed compositions, comprise:
a) from about 5 mg to about 15 mg by weight of CBD oil;
b) from about 5 mg to about 45 mg by weight of one or more edible oils; and
c) the balance one or more carriers.

In one embodiment of this aspect the disclosed compositions, comprise:
a) from about 5 mg to about 15 mg by weight of CBD oil;
b) from about 5 mg to about 45 mg by weight of one or more edible oils; and
c) from about 150 mg to about 500 mg by weight of one or more carriers.

In one iteration of this embodiment the disclosed compositions, comprise:
a) from about 5 mg to about 12 mg by weight of CBD oil;
b) from about 5 mg to about 30 mg by weight of one or more edible oils; and
c) from about 200 mg to about 350 mg by weight of one or more carriers.

In another iteration of this embodiment the disclosed compositions, comprise:
a) from about 7 mg to about 12 mg by weight of CBD oil;
b) from about 7 mg to about 24 mg by weight of one or more edible oils; and
c) from about 250 mg to about 350 mg by weight of one or more carriers.

In one non-limiting example the disclosed compositions, comprise:
a) from about 5 mg to about 15 mg by weight of CBD oil;
b) from about 5 mg to about 45 mg by weight of one or more edible oils; and
c) from about 200 mg to about 350 mg by weight of one or more carriers chosen from gum Arabic, inulin, or mixtures thereof.

In one non-limiting example the disclosed compositions, comprise:
a) from about 5 mg to about 15 mg by weight of CBD oil;
b) from about 5 mg to about 45 mg by weight of one or more edible oils;
c) from about 25 mg to about 45 mg by weight of one or more bile salts; and
d) from about 200 mg to about 350 mg by weight of one or more carriers chosen from gum Arabic, inulin, or mixtures thereof.

In a further non-limiting example the disclosed compositions, comprise:
a) about 10 mg by weight of CBD oil;
b) about 20 mg by weight of sunflower oil;
c) about 34 mg by weight of ox bile; and
c) about 278 mg by weight of gum Arabic.

In a further non-limiting example the disclosed compositions, comprise:
a) about 10 mg by weight of CBD oil;
b) about 20 mg by weight of coconut oil; and
c) about 240 mg by weight of inulin.

In a further aspect of the disclosed anti-hypertensive compositions, the composition comprise from about 5 mg to about 15 mg by weight of CBD oil. In one embodiment the base compositions can comprise from about 5 mg to about 12 mg by weight of CBD oil. In another embodiment the base compositions can comprise from about 7 mg to about 15 mg by weight of CBD oil. In further embodiment the base compositions can comprise from about 7 mg to about 12 mg by weight of CBD oil. The base compositions can comprise 5 mg, 6 mg, 7 mg, 8 mg, 9 mg, 10 mg, 11 mg, 12 mg, 13 mg, 14 mg, or 15 mg by weight of CBD oil.

Edible Oils

The disclosed compositions comprise one or more edible oils. The disclosed edible oils include oils that are primarily triglyceride-containing oils. Non-limiting examples of these oils are chosen from sunflower oil, coconut oil, canola oil, palm oil, soybean oil, corn oil, safflower oil, and peanut oil.

In another non-limiting example the edible oil is sunflower oil. In a further non-limiting example the edible oil is coconut oil. In a still further non-limiting example the edible oil is canola oil. In a yet further non-limiting example the edible oil is palm oil. In a still yet non-limiting example the edible oil is soybean oil. In another non-limiting example the edible oil is corn oil. In a still another non-limiting example the edible oil is safflower oil. In a yet another non-limiting example the edible oil is peanut oil.

The disclosed base compositions can comprise from about 0.5% to about 60% by weight of edible oil. In one embodiment the base compositions can comprise from about 3% to about 15% by weight of edible oil. In another embodiment the base compositions can comprise from about 5% to about 17% by weight of edible oil. In a further embodiment the base compositions can comprise from about 7.5% to about 15% by weight of edible oil. In a still further embodiment the base compositions can comprise from about 5% to about 10% by weight of edible oil. In a yet further embodiment the compositions comprise from about 20% to about 40% by weight of one or more edible oils. In a still yet further embodiment the compositions can comprise from about 15% to about 30% by weight of one or more edible oils.

The disclosed compositions can comprise from about 0.5% to about 60% by weight of one or more edible oils, for example, the amount of edible oil can be 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% by weight, or any fractional amount thereof, of one or more edible oils.

According to this aspect the ratio of CBD oil to edible oil is from about 1:1 to about 1:4. For example, the ratio of CBD oil to edible oil can be 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3.

The disclosed base compositions of this aspect comprise from about 5 mg to about 45 mg by weight of an edible oil. In one embodiment the base compositions can comprise from about 5 mg to about 30 mg by weight of one or more edible oils. In another embodiment the base compositions can comprise from about 5 mg to about 20 mg by weight of one or more edible oils. In a further embodiment the base compositions can comprise from about 5 mg to about 15 mg by weight of one or more edible oils. In a yet further embodiment the base compositions can comprise from about 5 mg to about 12 mg by weight of one or more edible oils. In a still further embodiment the base compositions can comprise from about 10 mg to about 30 mg by weight of one or more edible oils. In a yet another embodiment the base compositions can comprise from about 15 mg to about 25 mg by weight of one or more edible oils. The compositions can comprise 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, or 45 mg by weight of one or more edible oils.

The disclosed edible oils include oils that are primarily triglyceride-containing oils. Ono-limiting examples of these oils are chosen from sunflower oil, coconut oil, canola oil, palm oil, soybean oil, corn oil, safflower oil, and peanut oil.

In one non-limiting example, the pharmaceutical compositions comprise olive oil. In this example, high oleic acid olive oil can be used.

In another non-limiting example the edible oil is sunflower oil. In a further non-limiting example the edible oil is coconut oil. In a still further non-limiting example the edible oil is canola oil. In a yet further non-limiting example the edible oil is palm oil. In a still yet non-limiting example the edible oil is soybean oil. In another non-limiting example the edible oil is corn oil. In a still another non-limiting example the edible oil is safflower oil. In a yet another non-limiting example the edible oil is peanut oil.

In another aspect highly unsaturated carboxylic acids derived from plant-based triglycerides can be admixed with one or more edible oils. In this aspect, for example, a formulator having a base composition comprising 10% by weight of an edible oil, can substitute 5% of that edible oil with 5% of a disclosed carboxylic acid.

Carriers

In one aspect the disclosed carriers are polysaccharides. Non-limiting examples of poly saccharide carriers include inulin, galactogen, cellulose, chitin, pectin, psyllium, guar, hemicellulose, potato starch, and partially hydrolyzed polysaccharides. In another aspect the carriers are sugar alcohols, for example, sorbitol, erythritol, xylitol, lactitol, maltitol, mannitol, hydrogenated starch hydrolysates, isomaltose, or any combination thereof. In a further aspect carrier component is based on a native or chemically modified agar, alginates, carrageenan gum, cellulose, chitosan, chitin, cyclodextrin, dextran, gellan gum, glycogen, glycosaminoglycan, gum karaya, inulin, pectin, polydextrose, xanthan gum, or any other starches, gums or other polysaccharide, including functionalized derivatives, dextrinized, hydrolyzed, oxidized, alkylated, hydroxyalkylated, acetylated, fractionated, and physically modified starches and mixtures thereof. In some embodiments glycerin and/or propylene glycol can be added as a carrier.

In another aspect the carrier is chosen from gum Arabic, inulin, mannitol, silicon dioxide, colloidal silicon dioxide, microcrystalline cellulose, D-lactose monohydrate, tapioca starch, tapioca flour, quillaia, or mixtures thereof. In a further example the carrier is gum Arabic. In another example the carrier is inulin. In yet another example the carrier is microcrystalline cellulose. In a still further example the carrier is D-lactose monohydrate. In a still another example the carrier is quillaia. The carrier can be a combination of gum Arabic, inulin, microcrystalline cellulose, D-lactose monohydrate, or quillaia.

In one non-limiting example the carrier is mannitol, a non-limiting example is Partek™ mannitol, available from Partek Inc. In a further non-limiting example the carrier is a microcrystalline cellulose. In a still further example the carrier is colloidal silicon dioxide.

The disclosed base compositions can comprise from about 50% to about 99% by weight of one or more carriers. In one embodiment disclosed compositions can comprise from about 60% to about 95% by weight of one or more carriers. In another embodiment the disclosed compositions can comprise from about 60% to about 80% by weight of one or more carriers. In a yet another embodiment the disclosed compositions can comprise from about 75% to about 95% by weight of one or more carriers. In a further embodiment the disclosed compositions can comprise from about 65% to about 90% by weight of one or more carriers. As such, the disclosed base compositions can comprise 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of one or more carriers.

The disclosed base compositions can comprise from about 100 mg to about 500 mg by weight of one or more carriers. In one embodiment the base compositions comprise from about 250 mg to about 350 mg by weight of one or more carriers. In another embodiment the base compositions comprise from about 150 mg to about 300 mg by weight of one or more carriers. In a further embodiment the base compositions comprise from about 200 mg to about 300 mg by weight of one or more carriers. In a yet further embodiment the base compositions comprise from about 300 mg to about 400 mg by weight of one or more carriers. In one embodiment the base compositions comprise from about 200 mg to about 450 mg by weight of one or more carriers. The disclosed base compositions can comprise 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 490 mg, 491 mg, 492 mg, 493 mg, 494 mg, 495 mg, 496 mg, 497 mg, 498 mg, 499 mg, or 500 mg by weight of one or more carriers.

Bile Salts

The disclosed base compositions can further comprise from 5% to about 20% by weight of a bile salt. Bile salts enhance the ability of the disclosed compositions to target the duodenum. Non-limiting examples of bile salts and/or bile acids includes steroid acids (and/or the carboxylate anion thereof) and salts thereof, found in the bile of an animal (e.g., a human), including cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocholate, and the like. Taurocholic acid and/or taurocholate are referred to herein as TCA.

Bile salts are typically conjugated with glycine or taurine. For example, the term "bile acid" as used herein includes cholic acid conjugated with either glycine or taurine: glycocholate and taurocholate, respectively (and salts thereof). Any reference to a bile salt or bile acid used herein includes reference to an identical compound naturally or synthetically prepared. In one non-limiting example the bile salt is ox bile.

The disclosed compositions can comprise from about 5% to about 20% by weight of one or more bile salts. In one embodiment the compositions comprise from about 7.5% to about 20% by weight of one or more bile salts. In one embodiment the compositions comprise from about 7.5% to about 12.5% by weight of one or more bile salts. In one embodiment the compositions comprise from about 15% to about 20% by weight of one or more bile salts. In one embodiment the compositions comprise from about 5% to about 15% by weight of one or more bile salts. In one embodiment the compositions comprise from about 12% to about 15% by weight of one or more bile salts. The compositions can comprise, for example, 5%, 6%, 7%, 8%, 9%, 10%, 11%, 12%, 13%, 14%, 15%, 16%, 17%, 18%, 19%, or 20% by weight of one or more bile salts.

The disclosed compositions comprise from about 25 mg to about 50 mg by weight of one or more bile salts. In one embodiment, the compositions comprise from about 30 mg to about 50 mg by weight of one or more bile salts. In another embodiment, the compositions comprise from about 30 mg to about 40 mg by weight of one or more bile salts. In further embodiment, the compositions comprise from about 25 mg to about 40 mg by weight of one or more bile salts. In yet another embodiment, the compositions comprise from about 25 mg to about 35 mg by weight of one or more bile salts. The disclosed base compositions can comprise, for example, 25 mg, 26 mg, 27 mg, 28 mg, 29 mg, 30 mg 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg by weight one or more bile salts.

In a further aspect of the disclosed anti-hypertension composition comprises:
a) from about 10 mg to about 100 mg by weight of CBD oil;
b) from about 10 mg to about 300 mg by weight of sunflower oil; and
c) the balance one or more carriers.

In one embodiment of this aspect the base composition comprises:
a) from about 10 mg to about 100 mg by weight of CBD oil;
b) from about 10 mg to about 300 mg by weight of sunflower oil; and
c) from about 200 mg to about 800 mg by weight of one or more carriers.

In one non-limiting example of this embodiment the base compositions comprise:
a) from about 10 mg to about 100 mg by weight of CBD oil;
b) from about 10 mg to about 300 mg by weight of sunflower oil;
c) from about 50 mg to about 8 mg by weight of one ore more bile salts; and
d) from about 200 mg to about 800 mg by weight of one or more carriers.

In another non-limiting example of this embodiment the base compositions comprise:
a) from about 10 mg to about 100 mg by weight of CBD oil;
b) from about 10 mg to about 300 mg by weight of sunflower oil;
c) from about 50 mg to about 80 mg by weight of one ore more bile salts; and
d) from about 200 mg to about 800 mg by weight of one or more carriers wherein the carriers are chosen from tapioca starch, tapioca flour, silicon dioxide, and mixture thereof.

In another non-limiting example of this embodiment the base compositions comprise:
a) from about 25 mg to about 40 mg by weight of CBD oil;
b) from about 50 mg to about 80 mg by weight of sunflower oil;
c) from about 60 mg to about 70 mg by weight of one ore more bile salts; and
d) from about 500 mg to about 600 mg by weight of one or more carriers wherein the carriers are chosen from tapioca starch, tapioca flour, silicon dioxide, and mixture thereof.

In Further non-limiting example of this embodiment the base compositions comprise:
a) from about 75 mg to about 90 mg by weight of CBD oil;
b) from about 55 mg to about 70 mg by weight of sunflower oil;
c) from about 60 mg to about 70 mg by weight of one ore more bile salts; and
d) from about 500 mg to about 600 mg by weight of one or more carriers wherein the carriers are chosen from tapioca starch, tapioca flour, silicon dioxide, and mixture thereof.

In a still further non-limiting example of this embodiment the base compositions comprise:
a) about 81 mg by weight of CBD oil;
b) about 62 mg by weight of sunflower oil;
c) about 65 mg by weight of one ore more bile salts; and
d) about 575 mg by weight of one or more carriers wherein the carriers are chosen from tapioca starch, tapioca flour, silicon dioxide, and mixture thereof.

In another embodiment of this aspect the base composition comprises:
a) from about 20 mg to about 40 mg by weight of CBD oil;
b) from about 40 mg to about 80 mg by weight of sunflower oil; and
c) from about 500 mg to about 600 mg by weight of one or more carriers.

In one iteration of this embodiment the base composition comprises:
a) from about 70 mg to about 100 mg by weight of CBD oil;
b) from about 70 mg to about 200 mg by weight of sunflower oil; and
c) from about 300 mg to about 450 mg by weight of one or more carriers.

In one non-limiting example of this iteration the base composition comprises:
a) from about 70 mg to about 100 mg by weight of CBD oil;
b) from about 70 mg to about 200 mg by weight of sunflower oil; and
c) from about 300 mg to about 450 mg by weight of one or more carriers wherein the carriers are chosen from mannitol, silicon dioxide, colloidal silicon dioxide, microcrystalline cellulose, and mixture thereof.

In another non-limiting example of this iteration the base compositions comprise:
a) from about 80 mg to about 95 mg by weight of CBD oil;
b) from about 160 mg to about 190 mg by weight of sunflower oil; and
c) from about 300 mg to about 400 mg by weight of one or more carriers wherein the carriers are chosen from mannitol, silicon dioxide, colloidal silicon dioxide, microcrystalline cellulose, and mixture thereof.

In a further iteration the base compositions comprise:
a) from about 80 mg to about 95 mg by weight of CBD oil;
b) from about 160 mg to about 190 mg by weight of sunflower oil;
c) from about 60 mg to about 70 mg by weight of one ore more bile salts and
d) from about 300 mg to about 400 mg by weight of one or more carriers wherein the carriers are chosen from mannitol, silicon dioxide, colloidal silicon dioxide, microcrystalline cellulose, and mixture thereof.

In a still further non-limiting example of this iteration the base compositions comprise:
a) about 87 mg by weight of CBD oil;
b) about 174 mg by weight of sunflower oil;
c) about 65 mg by weight one or more bile salts; and
d) about 375 mg by weight of one or more carriers wherein the carriers are chosen from mannitol, silicon dioxide, colloidal silicon dioxide, microcrystalline cellulose.

In a still further embodiment of this aspect the base composition comprises:
a) from about 65 mg to about 85 mg by weight of CBD oil;
b) from about 135 mg to about 170 mg by weight of sunflower oil; and
c) from about 300 mg to about 400 mg by weight of one or more carriers.

In one iteration of this embodiment the base composition comprises:
a) from about 65 mg to about 85 mg by weight of CBD oil;
b) from about 135 mg to about 170 mg by weight of sunflower oil; and
c) from about 300 mg to about 400 mg by weight of one or more carriers wherein the carriers are chosen from mannitol, silicon dioxide, colloidal silicon dioxide, microcrystalline cellulose, and mixture thereof.

In one non-limiting example of this iteration the base composition comprises:
a) from about 70 mg to about 80 mg by weight of CBD oil;
b) from about 145 mg to about 160 mg by weight of sunflower oil; and
c) from about 300 mg to about 350 mg by weight of one or more carriers wherein the carriers are chosen from mannitol, silicon dioxide, colloidal silicon dioxide, microcrystalline cellulose, and mixture thereof.

In another non-limiting example of this iteration the base composition comprises:
a) from about 70 mg to about 80 mg by weight of CBD oil;
b) from about 145 mg to about 160 mg by weight of sunflower oil;
c) from about 5 mg to about 8 mg by weight of one or more bile salts; and
d) from about 300 mg to about 350 mg by weight of one or more carriers wherein the carriers are chosen mannitol, silicon dioxide, colloidal silicon dioxide, microcrystalline cellulose, and mixture thereof.

In a further non-limiting example of this iteration the base composition comprises:
a) about 76 mg by weight of CBD oil;
b) about 152 mg by weight of sunflower oil;
c) about 7 mg by weight of one or more bile salts; and
d) about 335 mg by weight of one or more carriers wherein the carriers are chosen from mannitol, silicon dioxide, colloidal silicon dioxide, microcrystalline cellulose, and mixture thereof.

In another example, a base composition comprises:
a) from about 5 mg to about 15 mg by weight of CBD oil;
b) from about 5 mg to about 60 mg by weight of an admixture of a carboxylic acids derived from a plant-based triglyceride and one or more edible oils, wherein the ratio of the carboxylic acid and the edible oils is from about 1:9 to about 9:1; and
c) from about 100 mg to about 300 mg by weight of one or more carriers.

Methods

Disclosed herein are methods for treating hypertension in a subject in need of treatment, comprising administering to the subject in need an effective amount of a composition defined herein above.

In one aspect of the disclosed method a total dosage of the disclosed composition is from about 90 mg to about 450 mg over the course of 24 hours depending upon the severity of the hypertension. For an average hum weighing 60 kg, this equates to from about 1.5 mg/kg to about 75 mg/kg per 24 hours.

In one embodiment the dosage per day is from about 90 mg to about 150 mg. In a further embodiment the dosage per day is from about 140 mg to about 250 mg. In another embodiment the dosage per day is from about 200 mg to about 400 mg. In a still further embodiment the dosage per day is from about 300 mg to about 450 mg. In a yet further embodiment the dosage per day is from about 250 mg to about 350 mg.

The dosage of one or more disclosed compositions can be from about 90 mg to about 450 mg per 24 hours, for example, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, or 450 mg per 24 hours.

Preparation Example 1

The following additions were made using a stainless-steel reaction vessel, paddle, and scrapper to assist in the formation of the admixtures. High oleic acid olive oil (90 g) was charged to a reaction vessel and stirred while heating to about 75° C. Cannabidiol (44.97 g, of a 99.378% sample) was combined with the high oleic acid olive oil and the admixture was stirred at about 75° C. until homogeneous. To a reaction vessel containing Aeroperl® 300 (80.62 g) was slowly added the cannabidiol/high oleic acid olive oil admixture with continuous and efficient stirring until homogeneous. Parteck-M® 100 mannitol (80.62 g) was added to the reaction mixture smith continuous stirring at 75° C. The contents of the vessel was spread evenly on a dehydrator tray and the tray was then placed in a convection air flow dehydrator at about 65° C. for 90 minutes. The trays were then allowed to cool to room temperature. The dehydrated admixture was transferred to stainless-steel vessel and deoxycholic acid (3.86 g) was added with continuous stirring until the admixture was homogeneous. The yield was of the total product was approximately 309 g. The composition for testing was formed into capsules having the quantities disclosed in Table 1.

The following additions were made using a stainless-steel reaction vessel, paddle, and scrapper to assist in the formation of the admixtures. Sunflower oil (25.52 g) was charged to a reaction vessel and stirred while heating to about 75° C. CBD oil (12.76 g, of a 78.33% sample) was melted at about 75° C. then combined with the sunflower oil and stirred for 2 hours then at stirred at 80° C. for 30 minutes with efficient stirring to produce a homogeneous admixture. To a second stainless-steel is charged gum Arabic (231.73 g). To the gum Arabic is added the CBD oil/sunflower oil admixture with efficient stirring. (Note the resulting admixture is clumpy and must be worked into a homogeneous state. The contents of the vessel was spread evenly on a dehydrator tray and the tray was then placed in a convection air flow dehydrator at about 65° C. for 90 minutes. After cooling, the admixture is sifted to break up any clumps. To a clean stainless-steel vessel is charged ox bile salt (30 g). To the ox bile salt the sifted admixture is added and the admixture is efficiently mixed for 20 minutes. The final admixture yields 284 g. The composition for testing was formed into capsules having the quantities disclosed in Table 5.

Animal Studies

TABLE 1

| Ingredients | % | mg |
|---|---|---|
| CBD oil[1] | 3.2 | 10 |
| Sunflower oil | 6.4 | 20 |
| Gum Arabic | 90.4 | 278 |
| Total | 100 | 308 |

[1]Contains 78.33% cannabidiol

TABLE 2

| Ingredients | % | mg |
|---|---|---|
| CBD oil[1] | 2.9 | 10 |
| Sunflower oil | 5.8 | 20 |
| Ox bile | 10 | 34.2 |
| Gum Arabic | 81.3 | 278 |
| Total | 100 | 342.2 |

[1]Contains 78.33% cannabidiol

TABLE 3

| Ingredients | % | mg |
|---|---|---|
| CBD oil[2] | 3.7 | 10 |
| Coconut oil | 7.4 | 20 |
| Inulin | 88.9 | 239.14 |
| Total | 100 | 269.14 |

[2]Contains 89.73% cannabidiol

Nanoemulsions

CBD oil (10 g) and sunflower oil (10 g) is combined with 100 g of D-lactose monohydrate to form a homogeneous admixture. The admixture is then metered into 212.5 gm of quillaja in 467.5 mL of water to form a pre-emulsion. The pre-emulsion is then passed through a high pressure microfluidizer homogenizer to afford the liquid nanoemulsion.

TABLE 4

| Ingredients | % | mg |
|---|---|---|
| Cannabidiol[3] | 6.5 | 10 |
| Sunflower oil | 6.6 | 10 |
| D-lactose monohydrate | 6.6 | 10 |
| quillaia | 25.8 | 37.5 |
| water | 54.4 | 83.5 |
| Total | 100 | 151 |

[3]Contains 99.65% cannabidiol

TABLE 5

| Ingredients | % | mg |
|---|---|---|
| CBD oil[3] | 6.5 | 10 |
| Sunflower oil | 6.6 | 10 |
| D-lactose monohydrate | 6.6 | 10 |
| quillaia | 25.8 | 37.5 |
| water | 54.4 | 83.5 |
| Total | 100 | 151 |

2. Contains 89.73% cannabidiol

Individual and Average Plasma Concentrations (ng/mL) and Pharmacokinetic Parameters for CBD after Oral Administration of the Composition of Table 1 at 25 mg/kg of CBD in Male Sprague-Dawley Rats (Group 1)

TABLE I

| | Animal number | | | | |
|---|---|---|---|---|---|
| Sample time (hr) | 1 | 2 | 3 | 4 | 5 |
| 0.033 | BLOQ | BLOQ | BLOQ | BLOQ | BLOQ |
| 0.067 | 1.71 | BLOQ | 0.549 | 2.70 | 1.22 |
| 0.1 | 3.01 | 2.84 | 1.84 | 6.40 | 4.07 |
| 0.13 | 539 | 3.69 | 3.85 | 12.0 | 7.52 |
| 2.0 | 21.7 | 8.39 | 10.2 | 20.2 | 17.7 |
| 0.25 | 37.4 | 13.0 | 22.3 | 31.5 | 37.0 |
| 0.5 | 116 | 62.6 | 39.6 | 59.4 | 62.8 |
| 0.75 | 191 | 95.0 | 73.7 | 55.2 | 79.4 |
| 1.0 | 174 | 84.2 | 75.9 | 53.4 | 80.4 |
| Dose (mg/kg) | 0.296 | 0.288 | 0.288 | 0.286 | 0.286 |
| Vol. dosed (mL) | 1.48 | 1.44 | 1.44 | 1.42 | 1.43 |
| $C_{max}$ (ng/mL) | 191 | 95.0 | 75.9 | 59.4 | 80.4 |
| $t_{max}$ (hr) | 0.75 | 0.75 | 1.0 | 0.5 | 1.0 |
| $t_{1/2}$ | ND[2] | ND[2] | ND[3] | ND[2] | ND[3] |
| $MRT_{last}$ (hr) | 0.697 | 0.699 | 0.696 | 0.616 | 0.653 |
| $AUC_{last}$ (hr · ng/mL) | 106 | 52.7 | 42.0 | 42.2 | 52.8 |
| $AUC_{\infty}$ (hr · ng/mL) | ND[3] | ND[2] | ND[3] | ND[2] | ND[3] |
| $AUC_{last}/D$ (hr · kg · ng/mL/mg) | 4.23 | 2.11 | 1.68 | 1.69 | 2.11 |
| $AUC_{\infty}/D$ (hr · kg · ng/mL/mg) | ND[3] | ND[2] | ND[3] | ND[2] | ND[3] |

1. Dose-normalized by dividing the parameter by the nominal dose in mg/kg.
[2]Not determined due to a lack of quantifiable data points trailing the Cmax.
[3]Not determined because the terminal elimination phase was not observed.
BLOQ = below the limit of quantitation (1 ng/mL)

TABLE II

| | Animal number | | | | |
|---|---|---|---|---|---|
| Sample time (hr) | 6 | 7 | 8 | 9 | 10 |
| 0.033 | BLOQ | BLOQ | BLOQ | 0.570 | 2.31 |
| 0.067 | 0.692 | BLOQ | 1.66 | 3.12 | 9.67 |
| 0.1 | 1.70 | 1.10 | 5.28 | 5.32 | 14.0 |
| 0.13 | 4.78 | 1.92 | 6.82 | 9.80 | 23.3 |
| 2.0 | 11.0 | 5.67 | 17.1 | 16.8 | 25.5 |
| 0.25 | 26.2 | 10.1 | 21.9 | 29.2 | 38.4 |
| 0.5 | 83.6 | 53.1 | 114 | 92.1 | 102 |
| 0.75 | 114 | 77.6 | 128 | 80.0 | 174 |
| 1.0 | 133 | 78.9 | 89.2 | 57.9 | 188 |
| Dose (mg/kg) | 0.300 | 0.289 | 0.286 | 0281 | 0.287 |
| Vol. dosed (mL) | 1.50 | 1.45 | 1.43 | 1.41 | 1.44 |
| $C_{max}$ (ng/mL) | 133 | 78.9 | 128 | 92.1 | 188 |
| $t_{max}$ (hr) | 1.0 | 1.0 | 0.75 | 0.50 | 1.0 |
| $t_{1/2}$ | ND[3] | ND[3] | ND[2] | ND[2] | ND[3] |
| $MRT_{last}$ (hr) | 0.699 | 0.708 | 0.660 | 0.623 | 0.696 |
| $AUC_{last}$ (hr · ng/mL) | 70.9 | 44.5 | 76.5 | 56.4 | 102 |
| $AUC_{\infty}$ (hr · ng/mL) | ND[3] | ND[3] | ND[2] | ND[2] | ND[3] |
| $AUC_{last}/D$ (hr · kg · ng/mL/mg) | 2.84 | 1.78 | 3.06 | 2.26 | 4.07 |
| $AUC_{\infty}/D$ (hr · kg · ng/mL/mg) | ND[3] | ND[3] | ND[2] | ND[2] | ND[3] |

1. Dose-normalized by dividing the parameter by the nominal dose in mg/kg.
[2]Not determined due to a lack of quantifiable data points trailing the Cmax.
[3]Not determined because the terminal elimination phase was not observed.
BLOQ = below the limit of quantitation (1 ng/mL)

TABLE III provides the mean and standard deviation for the results of Animals 1-10.

TABLE III

| Sample time (hr) | mean | SD |
|---|---|---|
| 0.033 | 1.44 | ND |
| 0.067 | 2.67 | 2.97 |
| 0.10 | 4.56 | 3.75 |
| 0.13 | 7.91 | 6.19 |
| 0.20 | 15.4 | 6.37 |
| 0.25 | 26.7 | 9.96 |
| 0.50 | 78.5 | 26.8 |
| 0.75 | 107 | 45.1 |
| 1.0 | 101 | 47.1 |
| Dose (mg/kg) | 0.289 | 0.005 |
| Vol. dosed (mL) | 1.45 | 0.03 |
| $C_{max}$ (ng/mL) | 112 | 46.6 |
| $t_{max}$ (hr) | 0.83 | 0.21 |
| $t_{1/2}$ | ND | ND |
| $MRT_{last}$ (hr) | 0.675 | 0.0341 |
| $AUC_{last}$ (hr · ng/mL) | 64.6 | 23.6 |
| $AUC_\infty$ (hr · ng/mL) | ND | ND |
| $AUC_{last}/D$ (hr · kg · ng/mL/mg) | 2.58 | 0.946 |
| $AUC_\infty/D$ (hr · kg · ng/mL/mg) | ND | ND |

Individual and Average Plasma Concentrations (ng/mL) and Pharmacokinetic Parameters for CBD after Oral Administration of the Composition of Table 2 at 25 mg/kg of CBD in Male Sprague-Dawley Rats (Group 2)

TABLE IV

| | Animal number | | | | |
|---|---|---|---|---|---|
| Sample time (hr) | 11 | 12 | 13 | 14 | 15 |
| 0.033 | BLOQ | BLOQ | BLOQ | BLOQ | BLOQ |
| 0.067 | 2.91 | 1.29 | 1.77 | 2.76 | BLOQ |
| 0.1 | 6.24 | 5.39 | 7.75 | 8.67 | 3.23 |
| 0.13 | 15.2 | 9.32 | 17.7 | 18.4 | 5.57 |
| 2.0 | 22.0 | 19.7 | 29.3 | 22.3 | 15.9 |
| 0.25 | 45.0 | 40.6 | 84.1 | 40.9 | 24.4 |
| 0.5 | 188 | 144 | 310 | 168 | 84.5 |
| 0.75 | 243 | 307 | 389 | 200 | 125 |
| 1.0 | 223 | 325 | 372 | 171 | 112 |
| Dose (mg/kg) | 0.297 | 0.287 | 0.282 | 0.287 | 0.293 |
| Vol. dosed (mL) | 149 | 1.44 | 141 | 1.44 | 1.47 |
| $C_{max}$ (ng/mL) | 243 | 325 | 389 | 200 | 125 |
| $t_{max}$ (hr) | 0.75 | 1.0 | 2.75 | 0.75 | 0.75 |
| $t_{1/2}$ | $ND^2$ | $ND^3$ | $ND^2$ | $ND^2$ | $ND^2$ |
| $MRT_{last}$ (hr) | 0.684 | 0.732 | 0.683 | 0.670 | 0.689 |
| $AUC_{last}$ (hr · ng/mL) | 145 | 161 | 237 | 122 | 71.4 |
| $AUC_\infty$ (hr · ng/mL) | $ND^2$ | $ND^3$ | $ND^2$ | $ND^2$ | $ND^2$ |
| $AUC_{last}/D$ (hr · kg · ng/mL/mg) | 5.79 | 6.45 | 9.47 | 4.89 | 2.85 |
| $AUC_\infty/D$ (hr · kg · ng/mL/mg) | $ND^2$ | $ND^3$ | $ND^2$ | $ND^2$ | $ND^2$ |

1. Dose-normalized by dividing the parameter by the nominal dose in mg/kg.
$^2$Not determined due to a lack of quantifiable data points trailing the Cmax.
$^3$Not determined because the terminal elimination phase was not observed.
BLOQ = below the limit of quantitation (1 ng/mL)

TABLE V

| | Animal number | | | | |
|---|---|---|---|---|---|
| Sample time (hr) | 16 | 17 | 18 | 18 | 20 |
| 0.033 | BLOQ | BLOQ | BLOQ | BLOQ | BLOQ |
| 0.067 | 5.89 | 5.94 | 2.05 | 2.64 | 4.42 |
| 0.1 | 17.0 | 15.1 | 6.86 | 6.53 | 6.01 |
| 0.13 | 23.6 | 24.8 | 10.4 | 12.6 | 14.0 |
| 2.0 | 38.7 | 47.1 | 20.7 | 27.3 | 23.1 |
| 0.25 | 71.4 | 79.4 | 49.2 | 45.7 | 45.2 |
| 0.5 | 156 | 339 | 105 | 93.2 | 99.8 |
| 0.75 | 120 | 434 | 155 | 128 | 191 |
| 1.0 | 92.0 | 316 | 133 | 123 | 106 |
| Dose (mg/kg) | 0.293 | 0.284 | 0.297 | 0.293 | 0.287 |
| Vol. dosed (mL) | 1.47 | 1.42 | 1.49 | 1.47 | 1.44 |
| $C_{max}$ (ng/mL) | 156 | 434 | 155 | 128 | 191 |
| $t_{max}$ (hr) | 0.50 | 0.75 | 0.75 | 0.75 | 0.75 |
| $t_{1/2}$ | $ND^2$ | $ND^2$ | $ND^2$ | $ND^3$ | $ND^2$ |
| $MRT_{last}$ (hr) | 0.596 | 0.670 | 0.670 | 0.664 | 0.669 |
| $AUC_{last}$ (hr · ng/mL) | 95.4 | 249 | 91.1 | 80.1 | 95.2 |
| $AUC_\infty$ (hr · ng/mL) | $ND^2$ | $ND^2$ | $ND^2$ | $ND^3$ | $ND^2$ |
| $AUC_{last}/D$ (hr · kg · ng/mL/mg) | 3.82 | 9.98 | 3.64 | 3.20 | 3.81 |
| $AUC_\infty/D$ (hr · kg · ng/mL/mg) | $ND^2$ | $ND^2$ | $ND^2$ | $ND^3$ | $ND^2$ |

1. Dose-normalized by dividing the parameter by the nominal dose in mg/kg.
$^2$Not determined due to a lack of quantifiable data points trailing the Cmax.
$^3$Not determined because the terminal elimination phase was not observed.
BLOQ = below the limit of quantitation (1 ng/mL)

TABLE VI provides the mean and standard deviation for the results of Animals 11-20.

TABLE VI

| Sample time (hr) | mean | SD |
|---|---|---|
| 0.033 | ND | ND |
| 0.067 | 3.30 | 1.72 |
| 0.10 | 8.28 | 4.36 |
| 0.13 | 15. | 6.13 |
| 0.20 | 26.6 | 9.56 |
| 0.25 | 52.6 | 19.2 |
| 0.50 | 169 | 89.3 |
| 0.75 | 229 | 113 |
| 1.0 | 197 | 105 |
| Dose (mg/kg) | 0.290 | 0.005 |
| Vol. dosed (mL) | 1.45 | 0.03 |
| $C_{max}$ (ng/mL) | 235 | 111 |
| $t_{max}$ (hr) | 0.75 | 0.12 |
| $t_{1/2}$ | ND | ND |
| $MRT_{last}$ (hr) | 0.673 | 0.0333 |
| $AUC_{last}$ (hr · ng/mL) | 135 | 63.7 |
| $AUC_\infty$ (hr · ng/mL) | ND | ND |
| $AUC_{last}/D$ (hr · kg · ng/mL/mg) | 5.39 | 2.55 |
| $AUC_\infty/D$ (hr · kg · ng/mL/mg) | ND | ND |

Individual and Average Plasma Concentrations (ng/mL) and Pharmacokinetic Parameters for CBD after Oral Administration of the Composition of Table 3 at 25 mg/kg of CBD in Male Sprague-Dawley Rats (Group 3)

TABLE VII

| | Animal number | | | | |
|---|---|---|---|---|---|
| Sample time (hr) | 21 | 22 | 23 | 24 | 25 |
| 0.033 | BOLQ | BOLQ | BOLQ | BOLQ | BOLQ |
| 0.067 | BOLQ | BOLQ | NS | BOLQ | BOLQ |

TABLE VII-continued

| Sample time (hr) | Animal number | | | | |
|---|---|---|---|---|---|
| | 21 | 22 | 23 | 24 | 25 |
| 0.1 | 0.72 | BOLQ | BOLQ | BOLQ | BOLQ |
| 0.13 | 1.15 | BOLQ | 0.597 | BOLQ | BOLQ |
| 2.0 | 2.55 | 0.516 | 1.61 | 0.918 | 1.66 |
| 0.25 | 3.25 | 0.884 | 2.60 | 1.71 | 3.56 |
| 0.5 | 5.44 | 2.15 | 9.37 | 13.8 | 20.5 |
| 0.75 | 12.2 | 6.08 | 11.8 | 24.3 | 28.9 |
| 1.0 | 16.1 | 7.19 | 15.2 | 31.3 | 32.6 |
| Dose (mg/kg) | 0.304 | 0.303 | 0.325 | 0.314 | 0.336 |
| Vol. dosed (mL) | 1.52 | 1.52 | 1.63 | 1.57 | 1.68 |
| $C_{max}$ (ng/mL) | 16.1 | 7.19 | 15.2 | 31.3 | 32.6 |
| $t_{max}$ (hr) | 1.0 | 1.0 | 1.0 | 1.0 | 1.0 |
| $t_{1/2}$ | $ND^2$ | $ND^2$ | $ND^2$ | $ND^2$ | $ND^2$ |
| $MRT_{last}$ (hr) | 0.719 | 0.752 | 0.701 | 0.747 | 0.716 |
| $AUC_{last}$ (hr · ng/mL) | 7.16 | 3.12 | 7.71 | 13.7 | 17.1 |
| $AUC_{\infty}$ (hr · ng/mL) | $ND^2$ | $ND^2$ | $ND^2$ | $ND^2$ | $ND^2$ |
| $AUC_{last}/D$ (hr · kg · ng/mL/mg) | 0.286 | 0.125 | 0.308 | 0.550 | 0.682 |
| $AUC_{\infty}/D$ (hr · kg · ng/mL/mg) | $ND^2$ | $ND^2$ | $ND^2$ | $ND^2$ | $ND^2$ |

1. Dose-normalized by dividing the parameter by the nominal dose in mg/kg.
$^2$Not determined due to a lack of quantifiable data points trailing the Cmax.
3. Not determined because the terminal elimination phase was not observed.
BLOQ = below the limit of quantitation (1 ng/mL)

TABLE VIII

| Sample time (hr) | Animal number | | | | |
|---|---|---|---|---|---|
| | 26 | 27 | 28 | 29 | 30 |
| 0.033 | BOLQ | BOLQ | BOLQ | BOLQ | BOLQ |
| 0.067 | BOLQ | BOLQ | 2.97 | BOLQ | BOLQ |
| 0.1 | BOLQ | BOLQ | 6.67 | 0.743 | BOLQ |
| 0.13 | 0.722 | BOLQ | 7.08 | 1.85 | 1.48 |
| 2.0 | 1.91 | 1.26 | 11.2 | 4.24 | 4346 |
| 0.25 | 2.99 | 2.48 | 14.4 | 6.97 | 7.60 |
| 0.5 | 7.86 | 13.3 | 18.0 | 16.4 | 33.7 |
| 0.75 | 16.5 | 28.9 | 42.9 | 16.5 | 38.4 |
| 1.0 | 15.3 | 35.8 | 26.6 | 21.8 | 39.1 |
| Dose (mg/kg) | 0.292 | 0.296 | 0.309 | 0.286 | 0287 |
| Vol. dosed (mL) | 1.46 | 1.48 | 1.55 | 1.43 | 1.44 |
| $C_{max}$ (ng/mL) | 16.5 | 35.8 | 42.9 | 21.8 | 39.1 |
| $t_{max}$ (hr) | 0.75 | 1.0 | 0.75 | 1.0 | 1.0 |
| $t_{1/2}$ | $ND^2$ | $ND^2$ | $ND^3$ | $ND^2$ | $ND^2$ |
| $MRT_{last}$ (hr) | 0.712 | 0754 | 0.652 | 0.663 | 0.682 |
| $AUC_{last}$ (hr · ng/mL) | 8.60 | 15.5 | 22.0 | 12.4 | 24.4 |
| $AUC_{\infty}$ (hr · ng/mL) | $ND^2$ | $ND^2$ | $ND^3$ | $ND^2$ | $ND^2$ |
| $AUC_{last}/D$ (hr · kg · ng/mL/mg) | 0.344 | 0.619 | 0.495 | 0.495 | 0.976 |
| $AUC_{\infty}/D$ (hr · kg · ng/mL/mg) | $ND^2$ | $ND^2$ | $ND^3$ | $ND^2$ | $ND^2$ |

1. Dose-normalized by dividing the parameter by the nominal dose in mg/kg.
$^2$Not determined due to a lack of quantifiable data points trailing the Cmax.
$^3$Not determined because the terminal elimination phase was not observed.
BLOQ = below the limit of quantitation (1 ng/mL)

TABLE XIX provides the mean and standard deviation for the results of Animals 21-30.

TABLE XIX

| Sample time (hr) | mean | SD |
|---|---|---|
| 0.033 | ND | ND |
| 0.067 | ND | ND |
| 0.10 | 2.72 | 3.42 |
| 0.13 | 2.20 | 2.44 |
| 0.20 | 3.03 | 3.15 |
| 0.25 | 4.64 | 4.04 |
| 0.50 | 14.1 | 8.98 |
| 0.75 | 22.6 | 12.1 |
| 1.0 | 24.1 | 10.6 |

TABLE XIX-continued

| Sample time (hr) | mean | SD |
|---|---|---|
| Dose (mg/kg) | 0.305 | 0.016 |
| Vol. dosed (mL) | 1.53 | 0.08 |
| $C_{max}$ (ng/mL) | 25.8 | 12.0 |
| $t_{max}$ (hr) | 0.95 | 0.11 |
| $t_{1/2}$ (hr) | ND | ND |
| $MRT_{last}$ (hr) | 0.710 | 0.0260 |
| $AUC_{last}$ (hr · ng/mL) | 13.2 | 6.78 |
| $AUC_{\infty}$ (hr · ng/mL) | ND | ND |
| $AUC_{last}/D$ (hr · kg · ng/mL/mg) | 0.527 | 0.271 |
| $AUC_{\infty}/D$ (hr · kg · ng/mL/mg) | ND | ND |

Individual and Average Plasma Concentrations (ng/mL) and Pharmacokinetic Parameters for CBD after Oral Administration of the Composition of Table 4 at 25 mg/kg of CBD in Male Sprague-Dawley Rats (Group 4)

TABLE X

| Sample time (hr) | Animal number | | | | |
|---|---|---|---|---|---|
| | 31 | 32 | 33 | 34 | 35 |
| 0.033 | BOLQ | BOLQ | BOLQ | BOLQ | 1.19 |
| 0.067 | 4.23 | 2.41 | 3.98 | 2.98 | 8.71 |
| 0.1 | 8.33 | 4.62 | 3.67 | 6.36 | 18.2 |
| 0.13 | 15.0 | 5.90 | 8.09 | 13.7 | 27.2 |
| 2.0 | 23.1 | 9.06 | 11.9 | 26.7 | 32.2 |
| 0.25 | 38.0 | 12.6 | 20.7 | 36.4 | 32.2 |
| 0.5 | 16.1 | 31.0 | 34.0 | 63.0 | 90.5 |
| 0.75 | 15.1 | 46.5 | 56.9 | 113 | 151 |
| 1.0 | 47.6 | 50.8 | 46.5 | 154 | 155 |
| Dose (mg/kg) | 0.281 | 0.291 | 0.284 | 0.292 | 0.283 |
| Vol. dosed (mL) | 1.41 | 1.46 | 1.42 | 1.46 | 1.42 |
| $C_{max}$ (ng/mL) | 47.6 | 50.8 | 56.9 | 154 | 155 |
| $t_{max}$ (hr) | 1.0 | 1.0 | 0.75 | 1.0 | 1.0 |
| $t_{1/2}$ | $ND^2$ | $ND^2$ | $ND^3$ | $ND^2$ | $ND^2$ |
| $MRT_{last}$ (hr) | 0.595 | 0.683 | 0.658 | 0.703 | 0.685 |
| $AUC_{last}$ (hr · ng/mL) | 37.0 | 28.7 | 33.0 | 71.3 | 88.8 |
| $AUC_{\infty}$ (hr · ng/mL) | $ND^2$ | $ND^2$ | $ND^3$ | $ND^2$ | $ND^2$ |
| $AUC_{last}/D$ (hr · kg · ng/mL/mg) | 1.48 | 1.15 | 1.32 | 2.85 | 3.55 |
| $AUC_{\infty}/D$ (hr · kg · ng/mL/mg) | $ND^2$ | $ND^2$ | $ND^3$ | $ND^2$ | $ND^2$ |

1. Dose-normalized by dividing the parameter by the nominal dose in mg/kg.
$^2$Not determined due to a lack of quantifiable data points trailing the Cmax.
$^3$Not determined because the terminal elimination phase was not observed.
BLOQ = below the limit of quantitation (1 ng/mL)

TABLE XI

| Sample time (hr) | Animal number | | | | |
|---|---|---|---|---|---|
| | 36 | 37 | 38 | 39 | 40 |
| 0.033 | 6.27 | BOLQ | 6.01 | 0.614 | BOLQ |
| 0.067 | 5.56 | 9.90 | 25.6 | 1.91 | 2.63 |
| 0.1 | 11.8 | 6.17 | 27.4 | 3.49 | 4.53 |
| 0.13 | 18.7 | 18.7 | 43.6 | 7.30 | 7.64 |
| 2.0 | 31.8 | 18.4 | 50.1 | 7.13 | 9.07 |
| 0.25 | 36.9 | 22.3 | 46.5 | 16.8 | 9.46 |
| 0.5 | 44.8 | 31.6 | 84.3 | 34.8 | 30.7 |
| 0.75 | 59.7 | 40.2 | 91.5 | 34.1 | 59.3 |
| 1.0 | 44.7 | 33.8 | 82.8 | 46.7 | 76.8 |
| Dose (mg/kg) | 0.279 | 0.267 | 0.287 | 0.284 | 0.279 |
| Vol. dosed (mL) | 1.40 | 1.34 | 1.44 | 1.42 | 1.40 |
| $C_{max}$ (ng/mL) | 59.7 | 40.2 | 91.5 | 46.7 | 76.8 |
| $t_{max}$ (hr) | 0.75 | 0.75 | 0.75 | 1.0 | 1.0 |
| $t_{1/2}$ | $ND^3$ | $ND^3$ | $ND^3$ | $ND^2$ | $ND^2$ |

TABLE XI-continued

| Sample time (hr) | Animal number | | | | |
| --- | --- | --- | --- | --- | --- |
| | 36 | 37 | 38 | 39 | 40 |
| $MRT_{last}$ (hr) | 0.598 | 0.603 | 0.597 | 0.653 | 0.724 |
| $AUC_{last}$ (hr · ng/mL) | 10.7 | 28.1 | 68.4 | 26.6 | 34.7 |
| $AUC_\infty$(hr · ng/mL) | ND[3] | ND[3] | ND[3] | ND[2] | ND[2] |
| $AUC_{last}/D$ (hr · kg · ng/mL/mg) | 1.63 | 1.12 | 2.74 | 1.06 | 1.39 |
| $AUC_\infty/D$ (hr · kg · ng/mL/mg) | ND[3] | ND[3] | ND[3] | ND[2] | ND[2] |

1. Dose-normalized by dividing the parameter by the nominal dose in mg/kg.
[2] Not determined due to a lack of quantifiable data points trailing the Cmax.
[3] Not determined because the terminal elimination phase was not observed.
BLOQ = below the limit of quantitation (1 ng/mL)

TABLE XII provides the mean and standard deviation for the results of Animals 31-40.

TABLE XII

| Sample time (hr) | mean | SD |
| --- | --- | --- |
| 0.033 | 2.11 | 2.61 |
| 0.067 | 6.79 | 7.13 |
| 0.10 | 9.46 | 7.76 |
| 0.13 | 16.6 | 11.6 |
| 0.20 | 21.9 | 13.7 |
| 0.25 | 27.2 | 12.5 |
| 0.50 | 49.1 | 22.6 |
| 0.75 | 69.7 | 37.4 |
| 1.0 | 73.9 | 45.0 |
| Dose (mg/kg) | 0.283 | 0.007 |
| Vol. dosed (mL) | 1.42 | 0.03 |
| $C_{max}$ (ng/mL) | 77.9 | 43.1 |
| $t_{max}$ (hr) | 0.90 | 0.13 |
| $t_{1/2}$ | ND | ND |
| $MRT_{last}$ (hr) | 0.650 | 0.0488 |
| $AUC_{last}$ (hr · ng/mL) | 45.7 | 22.0 |
| $AUC_\infty$(hr · ng/mL) | ND | ND |
| $AUC_{last}/D$ (hr · kg · ng/mL/mg) | 1.83 | 0.882 |
| $AUC_\infty/D$ (hr · kg · ng/mL/mg) | ND | ND |

Individual and Average Plasma Concentrations (ng/mL) and Pharmacokinetic Parameters for CBD after Oral Administration of the Composition of Table 5 at 25 mg/kg of CBD in Male Sprague-Dawley Rats (Group 5)

TABLE XIII

| Sample time (hr) | Animal number | | | | |
| --- | --- | --- | --- | --- | --- |
| | 41 | 42 | 43 | 44 | 45 |
| 0.033 | BOLQ | 0.521 | 1.59 | BOLQ | BOLQ |
| 0.067 | 4.50 | 5.30 | 8.02 | 3.11 | 5.35 |
| 0.1 | 16.5 | 14.1 | 17.5 | 3.14 | 9.37 |
| 0.13 | 20.7 | 19.3 | 26.4 | 5.72 | 20.1 |
| 2.0 | 521.0 | 39.5 | 56.5 | 9.71 | 37.5 |
| 0.25 | 31.7 | 55.0 | 61.0 | 14.5 | 45.6 |
| 0.5 | 72.9 | 92.3 | 81.4 | 63.8 | 101 |
| 0.75 | 84.1 | 116 | 93.2 | 42.2 | 102 |
| 1.0 | 77.8 | 114 | 93.1 | 68.3 | 127 |
| Dose (mg/kg) | 0.297 | 0.289 | 0.285 | 0.283 | 0.270 |
| Vol. dosed (mL) | 1.49 | 1.45 | 1.45 | 1.42 | 1.35 |
| $C_{max}$ (ng/mL) | 84.1 | 116 | 93.2 | 68.3 | 127 |
| $t_{max}$ (hr) | 0.75 | 0.75 | 0.75 | 1.0 | 1.0 |
| $t_{1/2}$ | ND[2] | ND[3] | ND[3] | ND[3] | ND[3] |
| $MRT_{last}$ (hr) | 0.639 | 0.640 | 0.607 | 0.657 | 0.647 |
| $AUC_{last}$ (hr · ng/mL) | 56.7 | 78.5 | 70.0 | 38.3 | 77.2 |

TABLE XIII-continued

| Sample time (hr) | Animal number | | | | |
| --- | --- | --- | --- | --- | --- |
| | 41 | 42 | 43 | 44 | 45 |
| $AUC_\infty$(hr · ng/mL) | ND[2] | ND[3] | ND[3] | ND[3] | ND[3] |
| $AUC_{last}/D$ (hr · kg · ng/mL/mg) | 2.27 | 3.14 | 2.80 | 1.53 | 3.09 |
| $AUC_\infty/D$ (hr · kg · ng/mL/mg) | ND[2] | ND[3] | ND[3] | ND[3] | ND[3] |

1. Dose-normalized by dividing the parameter by the nominal dose in mg/kg.
[2] Not determined due to a lack of quantifiable data points trailing the Cmax.
[3] Not determined because the terminal elimination phase was not observed.
BLOQ = below the limit of quantitation (1 ng/mL)

TABLE XIV

| Sample time (hr) | Animal number | | | | |
| --- | --- | --- | --- | --- | --- |
| | 46 | 47 | 48 | 49 | 50 |
| 0.033 | 2.34 | BLOQ | BLOQ | 0.950 | 3.04 |
| 0.067 | 8.58 | 3.37 | 1.26 | 4.25 | 17.1 |
| 0.1 | 14.2 | 5.85 | 3.18/ | 6.41 | 37.6 |
| 0.13 | 19.6 | 9.35 | 6.38 | 13.1 | 41.7 |
| 2.0 | 27.6 | 13.8 | 11.1 | 13.6 | 47.9 |
| 0.25 | 58.9 | 16.4 | 19.3 | 28.1 | 55.2 |
| 0.5 | 124 | 49.5 | 31.7 | 52.5 | 105 |
| 0.75 | 188 | 73.5 | 48.0 | 117 | 143 |
| 1.0 | 188 | 87.5 | 59.2 | 136 | 174 |
| Dose (mg/kg) | 0.274 | 0.288 | 0.283 | 0.278 | 0.277 |
| Vol. dosed (mL) | 1.37 | 1.44 | 1.42 | 1.39 | 1.39 |
| $C_{max}$ (ng/mL) | 188 | 87.5 | 59.2 | 136 | 174 |
| $t_{max}$ (hr) | 0.75 | 1.0 | 1.0 | 1.0 | 1.0 |
| $t_{1/2}$ | ND[2] | ND[3] | ND[3] | ND[3] | ND[3] |
| $MRT_{last}$ (hr) | 0.677 | 0.695 | 0.678 | 0.716 | 0.655 |
| $AUC_{last}$ (hr · ng/mL) | 114 | 45.7 | 31.4 | 65.4 | 98.9 |
| $AUC_\infty$(hr · ng/mL) | ND[2] | ND[3] | ND[3] | ND[3] | ND[3] |
| $AUC_{last}/D$ (hr · kg · ng/mL/mg) | 4.55 | 1.53 | 1.25 | 2.62 | 3.95 |
| $AUC_\infty/D$ (hr · kg · ng/mL/mg) | ND[2] | ND[3] | ND[3] | ND[3] | ND[3] |

1. Dose-normalized by dividing the parameter by the nominal dose in mg/kg.
[2] Not determined due to a lack of quantifiable data points trailing the Cmax.
[3] Not determined because the terminal elimination phase was not observed.
BLOQ = below the limit of quantitation (1 ng/mL)

TABLE XV provides the mean and standard deviation for the results of Animals 41-50.

TABLE XV

| Sample time (hr) | mean | SD |
| --- | --- | --- |
| 0.033 | 1.69 | 1.02 |
| 0.067 | 6.08 | 4.45 |
| 0.10 | 12.8 | 10.2 |
| 0.13 | 18.2 | 10.7 |
| 0.20 | 27.8 | 16.7 |
| 0.25 | 38.6 | 18.6 |
| 0.50 | 77.4 | 28.7 |
| 0.75 | 101 | 43.7 |
| 1.0 | 112 | 43.8 |
| Dose (mg/kg) | 0.282 | 0.008 |
| Vol. dosed (mL) | 1.42 | 0.04 |
| $C_{max}$ (ng/mL) | 116 | 43.3 |
| $t_{max}$ (hr) | 0.90 | 0.13 |
| $t_{1/2}$ | ND | ND |
| $MRT_{last}$ (hr) | 0.661 | 0.0312 |
| $AUC_{last}$ (hr · ng/mL) | 67.6 | 269.0 |
| $AUC_\infty$(hr · ng/mL) | ND | ND |
| $AUC_{last}/D$ (hr · kg · ng/mL/mg) | 2.70 | 1.04 |
| $AUC_\infty/D$ (hr · kg · ng/mL/mg) | ND | ND |

A Summary of the Average Plasma Exposures for CBD after Oral Administration of the Compositions Disclosed in Tables 1 to 8 at 25 mg/kg of CBD in Male Sprague-Dawley Rats

TABLE XVI

| Group | Test Composition | Cmax (ng/mL) | $t_{max}$ (hr) | $AUC_{last}$ (hr · ng/mL) | Dose-normalized $AUC_{last}$ (hr · kg · ng/mL/mg) |
|---|---|---|---|---|---|
| 1 | Table 1 | 112 | 0.83 | 64.6 | 2.58 |
| 2 | Table 2 | 235 | 0.75 | 135 | 5.39 |
| 3 | Table 3 | 25.8 | 0.95 | 13.2 | 0.527 |
| 4 | Table 4 | 77.9 | 0.90 | 15.7 | 1.83 |
| 5 | Table 5 | 113 | 0.90 | 67.6 | 2.70 |

A Summary of the Average Plasma Exposures for CBD after Oral Administration of the Composition Disclosed in Tables 1 to 5 at 25 mg/kg of CBD in Male Sprague-Dawley Rats

TABLE XVII

| Group | Test Composition | Cmax (ng/mL) | $t_{max}$ (hr) | $AUC_{last}$ (hr · ng/mL) | Dose-normalized $AUC_{last}$ (hr · kg · ng/mL/mg) |
|---|---|---|---|---|---|
| 1 | Table 1 | 112 | 0.83 | 64.6 | 2.58 |
| 2 | Table 2 | 235 | 0.75 | 135 | 5.39 |
| 3 | Table 3 | 25.8 | 0.95 | 13.2 | 0.527 |
| 4 | Table 4 | 77.9 | 0.90 | 15.7 | 1.83 |
| 5 | Table 5 | 113 | 0.90 | 67.6 | 2.70 |

Concentrations of CBD in Brain Tissue after Oral Administration of a Composition from Table 1 at 25 mg/kg of CBD in Male Sprague-Dawley Rats (Group 1)

TABLE XVII

| Time (hr) | Anim No. | Brain mass (g) | Brain homogenate volume (mL) | Brain homogenate conc. (ng/mL) | Brain tissue conc. (ng/g) | Mean (ng/g) | SD (ng/g) |
|---|---|---|---|---|---|---|---|
| 8.0 | 1 | 1.85 | 5.55 | 14.1 | 42.3 | 46.8 | 12.3 |
|  | 2 | 1.92 | 5.76 | 17.2 | 51.6 |  |  |
|  | 3 | 1.86 | 5.58 | 22.0 | 66.0 |  |  |
|  | 4 | 1.89 | 5.67 | 12.0 | 36.0 |  |  |
|  | 5 | 1.66 | 4.98 | 12.7 | 38.1 |  |  |
| 24 | 6 | 1.94 | 5.82 | 0.946 | 2.84 | 2.49 | 0.804 |
|  | 7 | 1.87 | 5.61 | 0.625 | 1.88 |  |  |
|  | 8 | 1.88 | 5.64 | 0.781 | 2.34 |  |  |
|  | 9 | 1.82 | 5.46 | 0.566 | 1.70 |  |  |
|  | 10 | 1.82 | 5.46 | 1.23 | 3.69 |  |  |

Concentrations of CBD in Brain Tissue after Oral Administration of the Composition of Table 2 at 25 mg/kg of CBD in Male Sprague-Dawley Rats (Group 2)

TABLE XIX

| Time (hr) | Anim No. | Brain mass (g) | Brain homogenate volume (mL) | Brain homogenate conc. (ng/mL) | Brain tissue conc. (ng/g) | Mean (ng/g) | SD (ng/g) |
|---|---|---|---|---|---|---|---|
| 8.0 | 21 | 1.88 | 5.64 | 48.8 | 146 | 275 | 155 |
|  | 22 | 1.82 | 5.46 | 130 | 390 |  |  |
|  | 23 | 1.77 | 5.31 | 38.1 | 114 |  |  |
|  | 24 | 1.88 | 5.64 | 93.6 | 251 |  |  |
|  | 25 | 1.78 | 5.34 | 158 | 474 |  |  |
| 24 | 26 | 1.92 | 5.76 | 2.78 | 8.34 | 6.21 | 2.00 |
|  | 27 | 1.69 | 5.07 | 2.21 | 6.63 |  |  |
|  | 28 | 1.92 | 5.76 | 2.48 | 7.44 |  |  |
|  | 29 | 1.86 | 5.58 | 1.82 | 5.46 |  |  |
|  | 30 | 1.84 | 5.52 | 1.06 | 3.18 |  |  |

Concentrations of CBD in Brain Tissue after Oral Administration of the Composition of Table 3 at 25 mg/kg of CBD in Male Sprague-Dawley Rats (Group 3)

TABLE XX

| Time (hr) | Anim No. | Brain mass (g) | Brain homogenate volume (mL) | Brain homogenate conc. (ng/mL) | Brain tissue conc. (ng/g) | Mean (ng/g) | SD (ng/g) |
|---|---|---|---|---|---|---|---|
| 8.0 | 41 | 1.94 | 5.82 | 3.36 | 10.1 | 13.5 | 9.11 |
|  | 42 | 1.92 | 5.76 | 3.32 | 10.0 |  |  |
|  | 43 | 2.04 | 6.12 | 1.77 | 5.31 |  |  |
|  | 44 | 1.86 | 5.58 | 4.46 | 13.4 |  |  |
|  | 45 | 2.12 | 6.36 | 9.67 | 29.0 |  |  |
| 24 | 46 | 1.74 | 5.22 | BLOQ | ND | ND | ND |
|  | 47 | 1.94 | 5.82 | BLOQ | ND |  |  |
|  | 48 | 1.92 | 5.76 | BLOQ | ND |  |  |
|  | 49 | 1.84 | 5.52 | BLOQ | ND |  |  |
|  | 50 | 1.99 | 5.97 | BLOQ | ND |  |  |

Concentrations of CBD in Brain Tissue after Oral Administration the Composition from Table 4 at 25 mg/kg of CBD in Male Sprague-Dawley Rats (Group 5)

TABLE XXI

| Time (hr) | Anim No. | Brain mass (g) | Brain homogenate volume (mL) | Brain homogenate conc. (ng/mL) | Brain tissue conc. (ng/g) | Mean (ng/g) | SD (ng/g) |
|---|---|---|---|---|---|---|---|
| 8.0 | 61 | 1.87 | 5.61 | 31.9 | 95.7 | 167 | 115 |
|  | 62 | 1.95 | 5.85 | 77.7 | 233 |  |  |
|  | 63 | 1.90 | 5.70 | 113 | 339 |  |  |
|  | 64 | 1.88 | 5.64 | 22.6 | 67.8 |  |  |
|  | 65 | 1.84 | 5.52 | 33.7 | 101 |  |  |

TABLE XXI-continued

| Time (hr) | Anim No. | Brain mass (g) | Brain homogenate volume (mL) | Brain homogenate conc. (ng/mL) | Brain tissue conc. (ng/g) | Mean (ng/g) | SD (ng/g) |
|---|---|---|---|---|---|---|---|
| 24 | 66 | 1.78 | 5.34 | 1.17 | 3.51 | 2.78 | 1.00 |
|  | 67 | 1.87 | 5.61 | 1.76 | 5.28 |  |  |
|  | 68 | 1.73 | 5.19 | 1.21 | 3.63 |  |  |
|  | 69 | 1.81 | 5.43 | 1.33 | 3.99 |  |  |
|  | 70 | 1.74 | 5.22 | 0.834 | 2.50 |  |  |

Concentrations of CBD in Brain Tissue after Oral Administration of the Composition of Table 5 at 25 mg/kg of CBD in Male Sprague-Dawley Rats (Group 5)

TABLE XXII

| Time (hr) | Anim No. | Brain mass (g) | Brain homogenate volume (mL) | Brain homogenate conc. (ng/mL) | Brain tissue conc. (ng/g) | Mean (ng/g) | SD (ng/g) |
|---|---|---|---|---|---|---|---|
| 8.0 | 71 | 1.79 | 5.37 | 38.9 | 117 | 142 | 38.3 |
|  | 72 | 4.91 | 5.73 | 42.9 | 129 |  |  |
|  | 73 | 1.94 | 5.82 | 70.1 | 210 |  |  |
|  | 74 | 1.74 | 5.22 | 42.2 | 127 |  |  |
|  | 75 | 1.79 | 5.37 | 43.2 | 130 |  |  |
| 24 | 76 | 1.86 | 5.58 | 1.94 | 5.82 | 5.33 | 0.703 |
|  | 77 | 2.04 | 6.12 | 1.62 | 4.86 |  |  |
|  | 78 | 1.94 | 5.82 | 1.78 | 5.34 |  |  |
|  | 79 | 1.94 | 5.82 | 1.48 | 4.44 |  |  |
|  | 80 | 1.92 | 5.76 | 2.06 | 6.18 |  |  |

Human Studies

The following compositions were used in controlled human clinical trials measuring the difference in systolic blood pressure (SBP), mean arterial pressure (MSP). and diastolic blood pressure (DBP) between volunteers taking a composition disclosed in Table 6 or Table 7 versus placebo over a 24 hour period.

TABLE 6

| Ingredients | Mass (mg) | Percent % |
|---|---|---|
| Cannabidiol oil[1] | 30.83 | 4.21 |
| High oleic acid sunflower oil | 61.67 | 8.41 |
| Tapioca starch | 492.50 | 67.1 |
| Ox bile extract[2] | 65.00 | 8.87 |
| Silicon dioxide | 18.00 | 2.69 |
| Tapioca flour | 65.00 | 8.87 |
| Total | 733.00 | 100 |

[1]contains 85.34% cannabidiol for an effective amount of 25 mg.
[2]contains 45-55% deoxycholic acid, taurocholate and glycocholic acid

TABLE 7

| Ingredients | Mass (mg) | Percent % |
|---|---|---|
| Cannabidiol oil[1] | 87.1 | 12.44 |
| High oleic acid sunflower oil | 174.20 | 24.89 |
| Tapioca starch | 164.84 | 23.55 |
| Aeroperl ® 300 | 158.86 | 22.69 |
| Ox bile extract[2] | 65.00 | 9.29 |
| Microcrystalline cellulose | 50.00 | 7.14 |
| Total | 700.00 | 100 |

[1]contains 90.64% cannabidiol for an effective amount of 75 mg.
[2]contains 45-55% deoxycholic acid, taurocholate and glycocholic acid The composition disclosed in Table 8 is used for a human clinical trial.

TABLE 8

| Ingredients | Mass (mg) | Percent % |
|---|---|---|
| Cannabidiol[1] | 75.76 | 13.29 |
| High oleic acid olive oil | 151.52 | 26.58 |
| Partek-M mannitol | 142.95 | 25.08 |
| Aeroperl ® 300 | 142.95 | 25.08 |
| Deoxycholic acid | 6.8 | 1.2 |
| Microcrystalline cellulose | 50.00 | 8.77 |
| Total | 570.00 | 100 |

[1]contains 99% cannabidiol for an effective amount of 75 mg.

Figure 11:
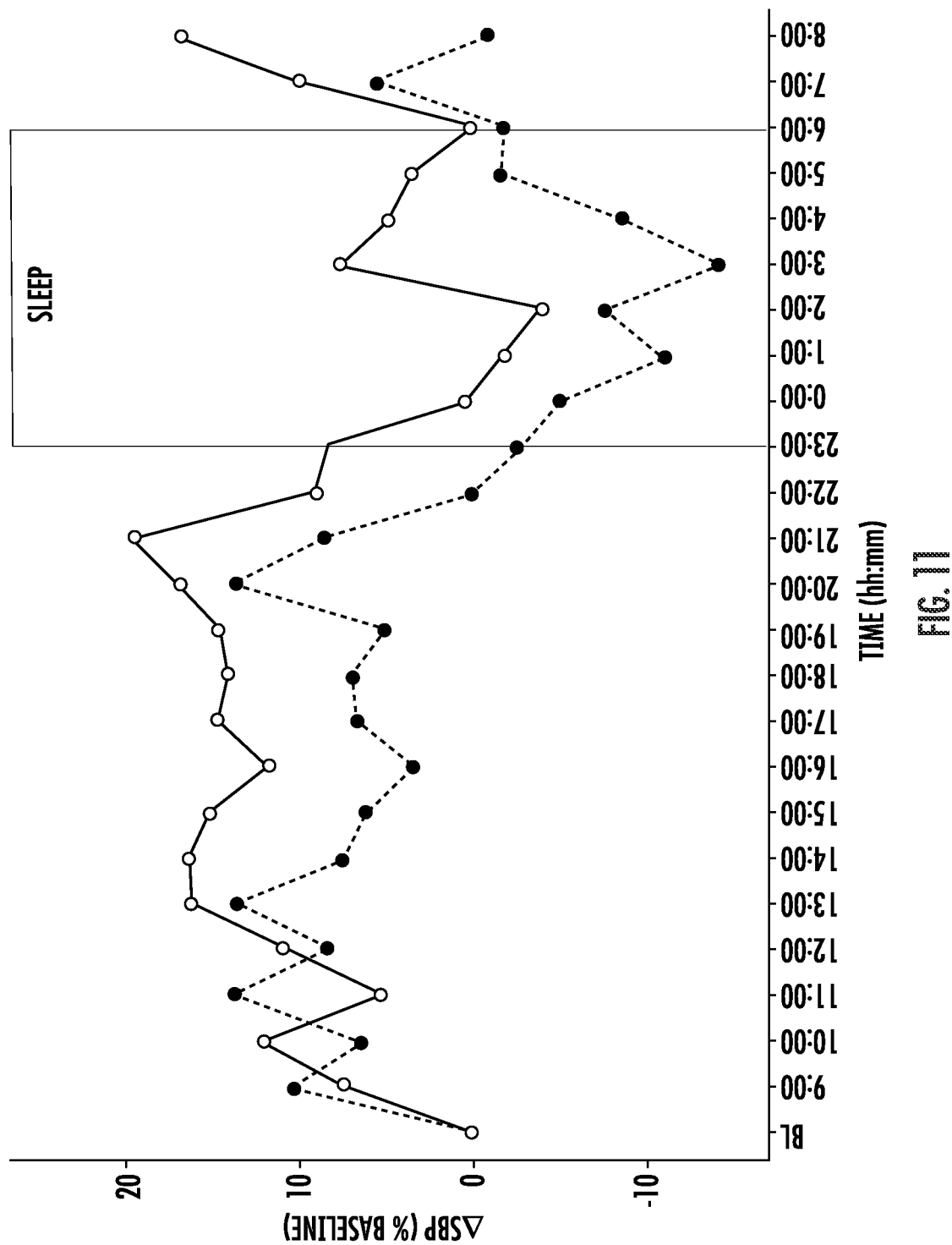
FIG. 11 is the 24-hour plot of the systolic blood pressure of subjects given the composition disclosed in Table 6 (●) versus placebo (○).

The composition disclosed in Table 6 was administered to human volunteers with mild to moderate hypertension under the following protocol. During a 24-hour study, 16 volunteers in each group were administered the composition of Table 6 or a placebo at selected times, t=0, t=13 hours, and t=22 hours. The results are depicted in FIG. 11. The results of subjects given the composition containing the composition in Table 6 are reflected in the dashed line with solid circles (●) and the subjects given the placebo are reflected in the solid line and open circles (○). As depicted in FIG. 11 the approximately 7% difference in systolic blood pressure (SBP) continued after the ambulatory period, i.e., during the sleep period.

Figure 12:
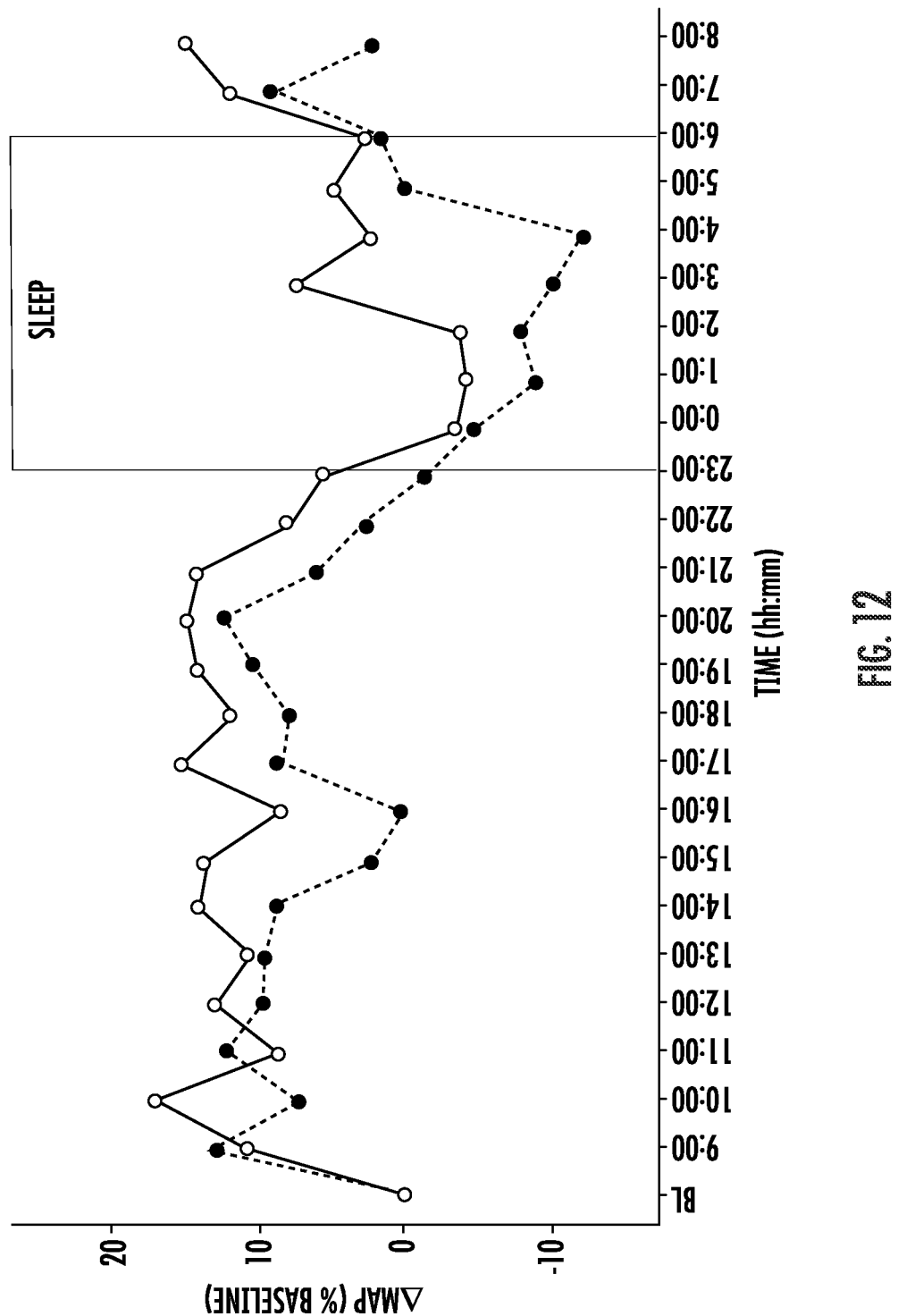
FIG. 12 is the 24-hour plot of the mean arterial pressure of subjects given the composition disclosed in Table 6 (●) versus placebo (○).
Figure 13:
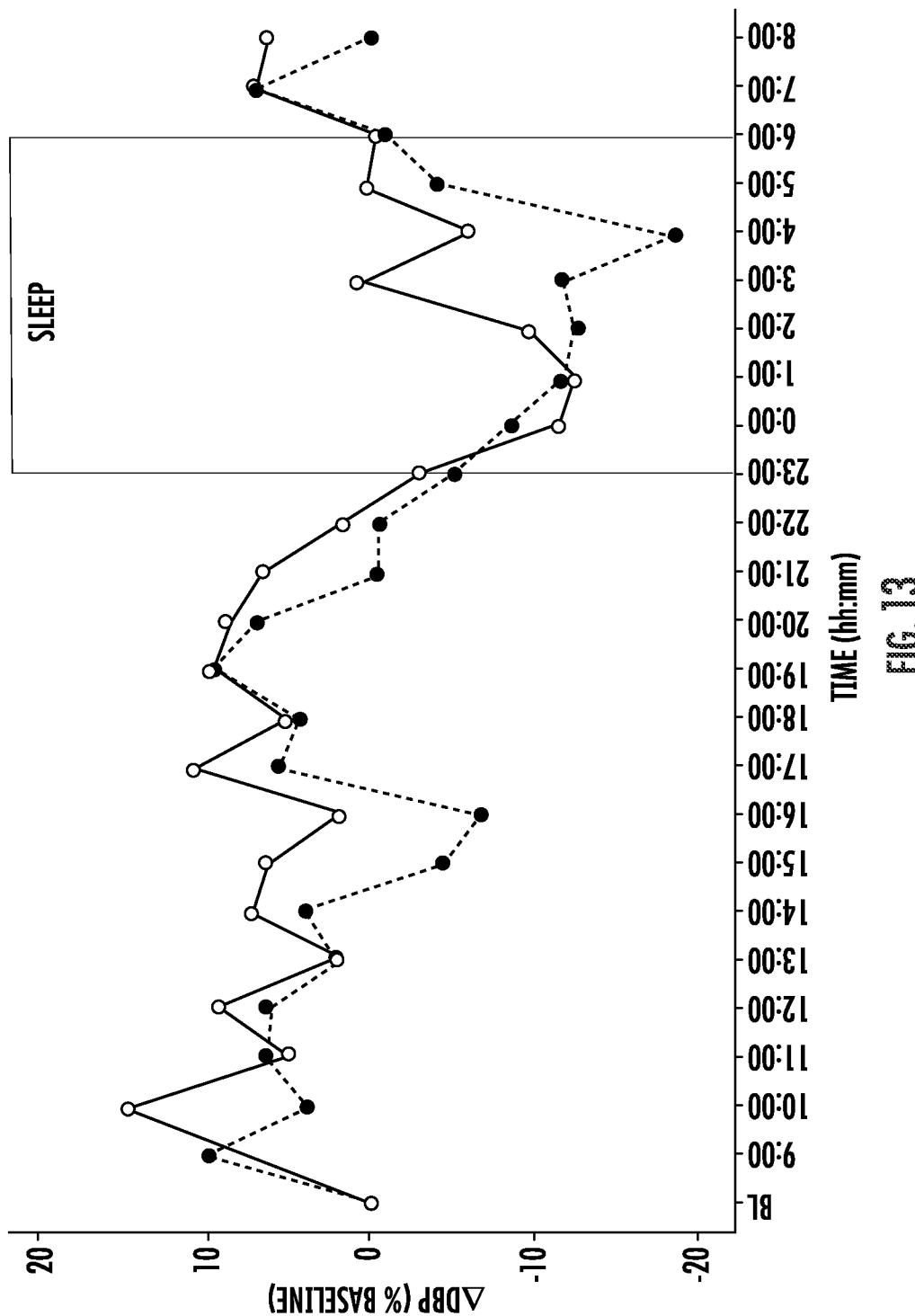
FIG. 13 is the 24-hour plot of the diastolic blood pressure of subjects given the composition disclosed in Table 6 (●) versus placebo (○).

FIG. 12 reflects the mean arterial pressures (MAP) of the two groups. During the ambulatory period, volunteers averaged a significant reduction of 5.3% in MAP versus the group given a placebo. FIG. 13 reflects the reduction of 3.5% in diastolic pressure versus placebo.

An analysis of the physical activity levels of the volunteers with mild to moderate hypertension during the 24-hour monitored period showed no significant differences in activity between the placebo and the composition from Table 6 treated volunteers, indicating that the observed differences in BP were not due to disparate physical movement or demands.

Arterial stiffness is a strong predictor of disease in humans. The impacts of increased arterial stiffness are not limited only to coronary heart disease such as hypertension, but also include other disease states such as diabetes mellitus, renal disease and more. It can also be a prognostic marker for cardiovascular events and all-cause mortality, even in asymptomatic individuals without overt cardiovascular disease.

The efficacy of blood pressure treatment and differences in efficacy between different types of antihypertensive agents is strongly correlated with measuring arterial stiffness, whereby the significant blood pressure reduction effects depicted in FIGS. 11 to 13 appear to have been at least partially due to these improvements in arterial stiffness. Arterial stiffness results from this study are summarized in Table XXIII below. All comparisons between the subject given the composition and placebo statistically significant (p<0.01).

TABLE XXII

| Measurement | Composition Table 6 | Placebo |
|---|---|---|
| Pulse Wave Velocity | 8.1 ± 0.3 m/s | 8..31 ± 0.3 m/s |
| Augmentation Index | 28.4 ± 1.4% | 32.3 ± 1.3% |
| Augmentation Index corrected to heart rate of 75 BPM | 27.8 ± 1.3% | 30.4 ± 1.3% |
| Augmentation pressure | 12.0 ± 1.0 mmHg | 14.6 ± 1.0 mmHg |

In this study 60 volunteers between the ages of 45-70 administering three 150 mg doses of the composition disclosed in Table 7, every day for 6-weeks. This study is a double blinded, randomized cross-over design, and utilizes a placebo control. Some volunteers are already using leading standard of care hypertension drugs such as ACE inhibitors with or without diuretics to assist in the evaluation of the composition disclosed in Table 7 to determine the efficacy of this composition with and without other hypertension treatments. The purpose of this study is to evaluate the potential for longer term health benefits.

This study is more comprehensive than the study conducted above and many types of analysis are performed including 24-hour ambulatory blood pressure (which is the primary outcome); arterial stiffness and autonomic balance; brain structure and function through brain magnetic resonance imaging ("MRI"); blood biomarkers (including lipids such as cholesterol and more); renal, hepatic, sleep quality/daytime sleepiness/sleep disorders; actigraphy, geriatric depression scale, perceived stress, and Beck anxiety inventory.

Other advantages which are obvious, and which are inherent to the disclosure will be evident to one skilled in the art. It will be understood that certain features and sub-combinations are of utility and may be employed without reference to other features and sub-combinations. This is contemplated by and is within the scope of the claims. Since many possible embodiments can be made relating to this disclosure without departing from the scope thereof, it is to be understood that all matter herein set forth or shown in the accompanying drawings is to be interpreted as illustrative and not in a limiting sense.

What is claimed is:

1. A method for treating hypertension in a subject in need of treatment, comprising administering to a subject in need an effective amount of a composition consisting of:
   a) from about 0.5% to about 20% by weight of CBD oil wherein the CBD oil contains from about 80% to about 92% by weight of cannabidiol;
   b) from about 0.5% to about 60% by weight of sunflower oil;
   c) from about 5% to about 20% by weight of a bile salt wherein the bile salt is selected from the group consisting of deoxycholic acid, taurocholate acid, glycocholic acid, or mixtures thereof; and
   (d) from about 50% to about 99% by weight of one or more carriers is selected from the group consisting of colloidal silicon dioxide, tapioca starch, or mixtures thereof.

2. The method according to claim 1, wherein the composition comprises from about 0.5% to about 8% by weight of CBD oil.

3. The method according to claim 1, wherein the composition comprises from about 1% to about 5% by weight of CBD oil.

4. The method according to claim 1, wherein the composition comprises from about 2% to about 5% by weight of CBD oil.

5. The method according to claim 1, wherein the composition comprises from about 2% to about 5% by weight of CBD oil.

6. The method according to claim 1, wherein the composition comprises from about 3% to about 15% by weight of CBD oil.

7. The method according to claim 1, wherein the composition comprises from about 5% to about 17% by weight of CBD oil.

8. The method according to claim 1, wherein the composition comprises from about 7.5% to about 15% by weight of sunflower oil.

9. The method according to claim 1, wherein the composition comprises from about 7.5% to about 12.5% by weight of a bile salt.

10. The method according to claim 1, wherein the composition comprises from about 60% to about 80% by weight of a carrier.

11. A method for treating hypertension in a subject in need of treatment, comprising administering to a subject in need an effective amount of a composition consisting of:
   a) from about 5 mg to about 15 mg by weight of CBD oil wherein the CBD oil contains from about 80% to about 92% by weight of cannabidiol;
   b) from about 5 mg to about 45 mg by weight of sunflower oil; and
   c) from about 1 mg to about 10 mg by weight of one or more bile salts wherein the bile salt is selected from the group consisting of deoxycholic acid, taurocholate, glycocholic acid or mixtures thereof; and
   d) one or more carriers selected from the group consisting of colloidal silicon dioxide, tapioca starch, or mixtures thereof.

12. The method according to claim 11, wherein the composition comprises from about 5 mg to about 12 mg by weight of CBD oil.

13. The method according to claim 11, wherein the composition comprises comprising from about 7 mg to about 12 mg by weight of CBD oil.

14. The method according to claim 11, wherein the composition comprises comprising from about 5 mg to about 30 mg by weight of sunflower oil.

15. The method according to claim 11, wherein the composition comprises comprising from about 5 mg to about 20 mg by weight of sunflower oil.

16. The method according to claim 11, wherein the composition comprises comprising from about 5 mg to about 12 mg by weight of sunflower oil.

17. A method for treating hypertension in a subject in need of treatment, comprising administering to a subject in need an effective amount of a composition consisting of:
   a) from about 10 mg to about 100 mg by weight of CBD oil wherein the CBD oil contains from about 80% to about 92% by weight of cannabidiol;
   b) from about 10 mg to about 300 mg by weight of sunflower oil; and
   c) from about 60 mg to about 70 mg by weight of one or more bile salts wherein the bile salt is selected from the group consisting of deoxycholic acid, taurocholate, glycocholic acid or mixtures thereof; and d) from about 200 mg to about 800 mg by weight of one or more carriers selected from the group consisting of tapioca starch, tapioca flour, silicon dioxide, and mixtures thereof.

18. The method according to claim 17, wherein the composition consists of:
    a) from about 25 mg to about 40 mg by weight of CBD oil wherein the CBD oil contains from about 80% to about 92% by weight of cannabidiol;
    b) from about 50 mg to about 80 mg by weight of sunflower oil; and
    c) from about 60 mg to about 70 mg by weight of one or more bile salts wherein the bile salt is selected from the group consisting of deoxycholic acid, taurocholate, glycocholic acid or mixtures thereof; and
    d) from about 500 mg to about 600 mg by weight of one or more carriers selected from the group consisting of tapioca starch, tapioca flour, silicon dioxide, and mixtures thereof.

19. The method composition according to claim 17, consisting of wherein the composition consists of:
    a) from about 75 mg to about 90 mg by weight of CBD oil wherein the CBD oil contains from about 80% to about 92% by weight of cannabidiol;
    b) from about 55 mg to about 80 mg by weight of sunflower oil; and
    c) from about 60 mg to about 70 mg by weight of one or more bile salts wherein the bile salt is selected from the group consisting of deoxycholic acid, taurocholate, glycocholic acid or mixtures thereof; and
    d) from about 500 mg to about 600 mg by weight of one or more carriers selected from the group consisting of tapioca starch, tapioca flour, silicon dioxide, and mixtures thereof.

20. The method composition according to claim 17, consisting of wherein the composition consists of:
    a) about 81 mg by weight of CBD oil wherein the CBD oil contains from about 80% to about 92% by weight of cannabidiol;
    b) about 62 mg by weight of sunflower oil; and
    c) about 65 mg by weight of one or more bile salts wherein the bile salt is selected from the group consisting of deoxycholic acid, taurocholate, glycocholic acid or mixtures thereof; and
    d) about 575 mg by weight of one or more carriers selected from the group consisting of tapioca starch, tapioca flour, silicon dioxide, and mixtures thereof.

* * * * *